(12) United States Patent
Metcalf et al.

(10) Patent No.: US 11,713,472 B2
(45) Date of Patent: Aug. 1, 2023

(54) GENOME EDITING IN ARCHAEA

(71) Applicant: The Board of Trustees of the University of Illinois, Urbana, IL (US)

(72) Inventors: William W. Metcalf, Savoy, IL (US); Dipti Dinkar Nayak, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 618 days.

(21) Appl. No.: 16/291,479

(22) Filed: Mar. 4, 2019

(65) Prior Publication Data

US 2019/0276854 A1    Sep. 12, 2019

Related U.S. Application Data

(60) Provisional application No. 62/639,344, filed on Mar. 6, 2018.

(51) Int. Cl.
| | |
|---|---|
| *C12N 15/90* | (2006.01) |
| *C12N 15/10* | (2006.01) |
| *C12N 15/82* | (2006.01) |
| *C12N 15/63* | (2006.01) |

(52) U.S. Cl.
CPC ......... *C12N 15/902* (2013.01); *C12N 15/102* (2013.01); *C12N 15/63* (2013.01); *C12N 15/8213* (2013.01); *C12N 2310/20* (2017.05)

(58) Field of Classification Search
None
See application file for complete search history.

(56) References Cited

U.S. PATENT DOCUMENTS

2014/0068797 A1    3/2014    Doudna

OTHER PUBLICATIONS

Danner et al., "Characterization of the distal promoter element of halobacteria in vivo using saturation mutagenesis and selection" 19(6) Molecular Microbiology 1265-1276 (Year: 1996).*
Gophna et al., "Finally, Archaea Get Their CRISPR-Cas Toolbox", Trends in Microbiology, 25(6):430-432 (2017).
Bartlett et al., "Ribonucleolytic resection is required for repair of strand displaced nonhomologous end-joining intermediates", Proc Natl Acad Sci USA, 110(22):E1984-E1991 (2013).
Bartlett et al., "Molecular basis for DNA strand displacement by NHEJ repair polymerases", Nucleic Acids Research, 44(5):2173-2186 (2016).
Wang et al., "Genetic screens in human cells using the CRISPR/Cas9 system", Science, 343(6166):80-84 (2014).
Nayak et al., "Cas9-mediated genome editing in the methanogenic archaeon Methanosarcina acetivorans", Proc Natl Acad Sci USA, 114(11):2976-2981 (2017).
Guss et al., "Genetic analysis of mch mutants in two Methanosarcina speices demonstrates multiple roles for the methanopterin-dependent C-1 oxidation/reduction pathway and differences in H2 metabolism between closely related species", Molecular Microbiology, 55(6):1671-1680 (2005).
Guss et al., "New methods for tightly regulated gene expression and highly efficient chromosomal integration of cloned genes for Methanosarcina species", Archaea, 2:193-203 (2008).
Pritchett et al., "Development of a Markerless Genetic Exchange Method for Methanosarcina acetivorans C2A and Its Use in Construction of a New Genetic Tools for Methanogenic Archaea", Applied and Environmental Microbiology, 70(3):1425-1433 (2004).
Rother et al., "Methanol-Dependent Gene Expression Demonstrates that Methyl-Coenzyme M Reductase is Essential in Methanosarcina acetivorans C2A and Allows Isolation of Mutants with Defects in Regulation of the Methanol Utilization Pathway", Journal of Bacteriology, 187(16):5552-5559 (2005).
Buan et al., "Methanogenesis by Methanosarcina acetivorans involves two structurally and functionally distinct classes of heterodisulfide reductase", Molecular Microbiology, 75(4):843-853 (2010).
Galagan et al., "The Genome *M. acetivorans* Reveals Extensive Metabolic and Physiological Diversity", Genome Research, 12:532-542 (2002).
Nayak, "CRISPR-Cas9 genome editing in the methanogenic archaeon Methanosarcina acetivorans C2A", Presentation dated Apr. 28, 2016.
Nayak et al., "Cas9 mediated genome editing of the methanogenic archaeon Methanosarcina acetivorans C2A", Poster (2016).

* cited by examiner

*Primary Examiner* — Nancy J Leith
(74) *Attorney, Agent, or Firm* — Lathrop GPM LLP; Lisa Hillman

(57) ABSTRACT

Methods of RNA-guided DNA endonuclease-mediated genome editing in Bacteria and Archaea are provided.

13 Claims, 11 Drawing Sheets
(11 of 11 Drawing Sheet(s) Filed in Color)
Specification includes a Sequence Listing.

A

```
AAG GAA GAA GCT CGA AGA CCT GG  .......... (spacer + PAM for mtmB1)
|||  |||  |||  |||  |||  |||  || |
AAG GAA GAA GCT CGA AGA ACT AG  .......... (mtmB2 CDS)

AGGT TGC GCA CAG TTA GCC CAG G  .......... (spacer + PAM for mtmC1)
|||  ||  |   ||| |||  ||||| |
AGGC TGT GTA CAG TTA ACC CAG G  .......... (mtmC2 CDS)
```

B

```
CTG AGG CAG AAA GAT CTC TGC GG  .......... (spacer + PAM for mtmB2)
||| |||  |  ||| |||  || |
CTG AGG TAG AAA GAC CCT CAG CA  .......... (mtmB1 CDS)

GAG GAG GCA CAT CTC CGT ACC GG  .......... (spacer + PAM for mtmC2)
 || ||| ||| ||| |||  |||| |
AAG GAG GCA CAT CTC TGT ACA TG  .......... (mtmC1 CDS)
```

Fig. 8

GENOME EDITING IN ARCHAEA

PRIORITY

This application claims the benefit of U.S. provisional application Ser. No. 62/639,344, filed on Mar. 6, 2018, which is incorporated by reference herein in its entirety.

STATEMENT REGARDING FEDERALLY SPONSORED RESEARCH OR DEVELOPMENT

This invention was made with government support under DE-FG02-02ER15296 awarded by the Department of Energy. The government has certain rights in the invention.

SEQUENCE LISTING

This document incorporates by reference a sequence listing named 19_089.SL1.txt, created on Mar. 4, 2019, which is 10,607 bytes in size.

BACKGROUND

CRISPR-Cas technologies are needed in the art for archaeal organisms because Archaea are difficult to study with traditional genome manipulation techniques. CRISPR-Cas technologies that can be used in Archaea would be extremely useful.

SUMMARY OF THE INVENTION

Provided herein are genetic engineering cassettes. A genetic engineering cassette can comprise a first Euyarchaeota promoter operably linked to one or more sgRNA sequences, a homologous recombination editing template comprising two homology arms with a deletion portion, a substitution portion, or an insertion portion between the two homology arms, wherein the two homology arms have homology to a Euyarchaeota nucleic acid molecule. The deletion portion, the substitution portion, or the insertion portion between the two homology arms can further comprise a restriction endonuclease site. The first Euyarchaeota promoter can be a methanogen promoter, and the Euyarchaeota nucleic acid molecule can be a methanogen nucleic acid molecule.

Another embodiment provides a vector comprising a genetic engineering cassette described herein and further comprising a nucleic acid molecule encoding an RNA-guided DNA endonuclease protein operably linked to a second Euyarchaeota promoter. The second Euyarchaeota promoter can be a methanogen promoter. The vector can further comprise a Euyarchaeota or methanogen origin of replication. The vector can further comprise a selection marker, a counter-selection marker, or both a selection marker and a counter-selection marker.

Yet another embodiment provides a method of homology directed repair-assisted engineering in a Euyarchaeota. The method comprises delivering one or more vectors described herein to Euyarchaeota host cells and isolating transformed Euyarchaeota host cells. The one or more vectors can comprise a counter-selectable marker and the method can further comprise curing the transformed Euyarchaeota host cells of the one or more vectors by subjecting the transformed Euyarchaeota host cells to a counter-selection technique. The RNA-guided DNA endonuclease can comprise a bacterial Cas 9 protein.

Still another embodiment provides a method for testing for gene essentiality. The method comprises delivering one or more vectors comprising (i) a first Euyarchaeota promoter operably linked to one or more sgRNA sequences that target a specific Euyarchaeota gene, and (ii) a nucleic acid molecule encoding an RNA-guided DNA endonuclease protein operably linked to a second Euyarchaeota promoter, to a first set of Euyarchaeota host cells to generate a first set of transformed cells. One or more vectors targeting the specific Euyarchaeota gene are delivered to a second set of Euyarchaeota host cells The one or more vectors comprise (i) a third Euyarchaeota promoter operably linked to one or more sgRNA sequences, (ii) a homologous recombination editing template comprising two homology arms with a deletion portion, a substitution portion, or an insertion portion between the two homology arms, wherein the two homology arms have homology to a Euyarchaeota nucleic acid molecule, and (iii) a nucleic acid molecule encoding an RNA-guided DNA endonuclease protein operably linked to a fourth Euyarchaeota promoter. A second set of transformed cells is generated. The ratio of a number of cells in the first set of transformed cells to a number of cells in the second set of transformed cells is determined.

Another embodiment provides a vector comprising a genetic engineering cassette. The genetic engineering cassette can comprise (i) nucleic acid molecules encoding a methanogen DNA ligase, a methanogen polymerase, a methanogen phosphoesterase, and a methanogen Ku protein, wherein the nucleic acid molecules are operably linked to one or more first methanogen promoters, (ii) a second methanogen promoter operably linked to one or more sgRNA sequences, and (iii) a third methanogen promoter operably linked to a nucleic acid molecule encoding a RNA-guided DNA endonuclease protein.

Still another embodiment provides a method of deleting all or part of a nucleic acid molecule in methanogen cells or a bacterial cells comprising delivering the one or more vectors described above to methanogen cells or bacterial cells, and isolating transformed methanogen cells or bacterial cells.

Yet another embodiment provides a method of generating a pool of mutated methanogen cells or bacterial cells, wherein the mutated methanogen cells or bacterial cells have two or more different mutations of a target site. The method comprises delivering the one or more vectors described above to methanogen cells or bacterial cells, and isolating transformed methanogen cells or bacterial cells.

The nucleic acid molecules encoding a methanogen DNA ligase, a methanogen polymerase, a methanogen phosphoesterase, and a methanogen Ku protein can be present in an operon.

Although RNA-guided DNA endonuclease-mediated genome editing has proven to be a powerful genetic tool in eukaryotes, its application in Bacteria has been limited due to inefficient targeting and/or repair; and its application to Archaea has yet to be reported. Provided herein are RNA-guided DNA endonuclease-mediated genome editing tools that allow facile genetic manipulation of Archaea, such as the slow-growing methanogenic *Methanosarcina acetivorans* and Halobacteria. Introduction of both insertions and deletions by homology directed repair (HDR) is remarkably efficient and precise, with the desired mutation being found in essentially all transformants examined. Off-target activity was not observed. Multiple sgRNAs can be expressed in the same transcript, reducing the size of mutagenic plasmids and simultaneously simplifying their design. RNA-guided DNA endonuclease-mediated genome editing reduces the time needed to construct mutants by more than half (three weeks versus eight weeks) and allows simultaneous construction of double mutants with high efficiency, exponentially decreasing the time needed for complex strain constructions. Furthermore, co-expression NHEJ machinery from Archaea (e.g., *Methanocella paludicola*), allows for efficient RNA-guided DNA endonuclease-mediated genome editing without the need for a repair template. NHEJ-dependent mutations can produce various sized deletions, most of which occur at regions of naturally-occurring microhomology. The combination of HDR-dependent and NHEJ-dependent genome-editing tools comprises a powerful genetic system that enables facile insertion and deletion of genes, rational modification of gene expression, and testing of gene essentiality.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 8 shows homology between target sequences for mtmCB1 and mtmCB2. (A) Alignment of the spacer and the PAM (underlined) for mtmB1 and mtmC1 with the corresponding regions in the mtmB2 and mtmC2 CDS, respectively. Spacer+PAM for mtmB1 is SEQ ID NO:40; mtmB2 CDS is SEQ ID NO:41; spacer+PAM for mtmC1 is SEQ ID NO:42; mtmC2 CDS is SEQ ID NO:43. (B) Alignment of the spacer and the PAM (underlined) for mtmB2 and mtmC2 with the corresponding regions in the mtmB1 and mtmC1 CDS. Spacer+PAM for mtmB2 is SEQ ID NO:44; mtmB1 CDS is SEQ ID NO:45; spacer+PAM for mtmC2 is SEQ ID NO:46; mtmC1 CDS is SEQ ID NO:47.

DETAILED DESCRIPTION

Methanogenic archaea play a central role in the global carbon cycle, with profound implications for climate change, yet our knowledge regarding the biology of these important organisms leaves much to be desired. A key bottleneck that hinders the study of Archaea, especially those within the genus *Methanosarcina*, results from the time-consuming and often cumbersome tools that are currently available for genetic analysis of these microbes. The Cas9-mediated genome editing approach for Archaea described in this study addresses this major constraint by streamlining the mutagenic process and enabling simultaneous introduction of multiple mutations. This work also sheds light on the distinct properties of homology-dependent repair and non-homologous end-joining machinery in Archaea.

Figure 1:
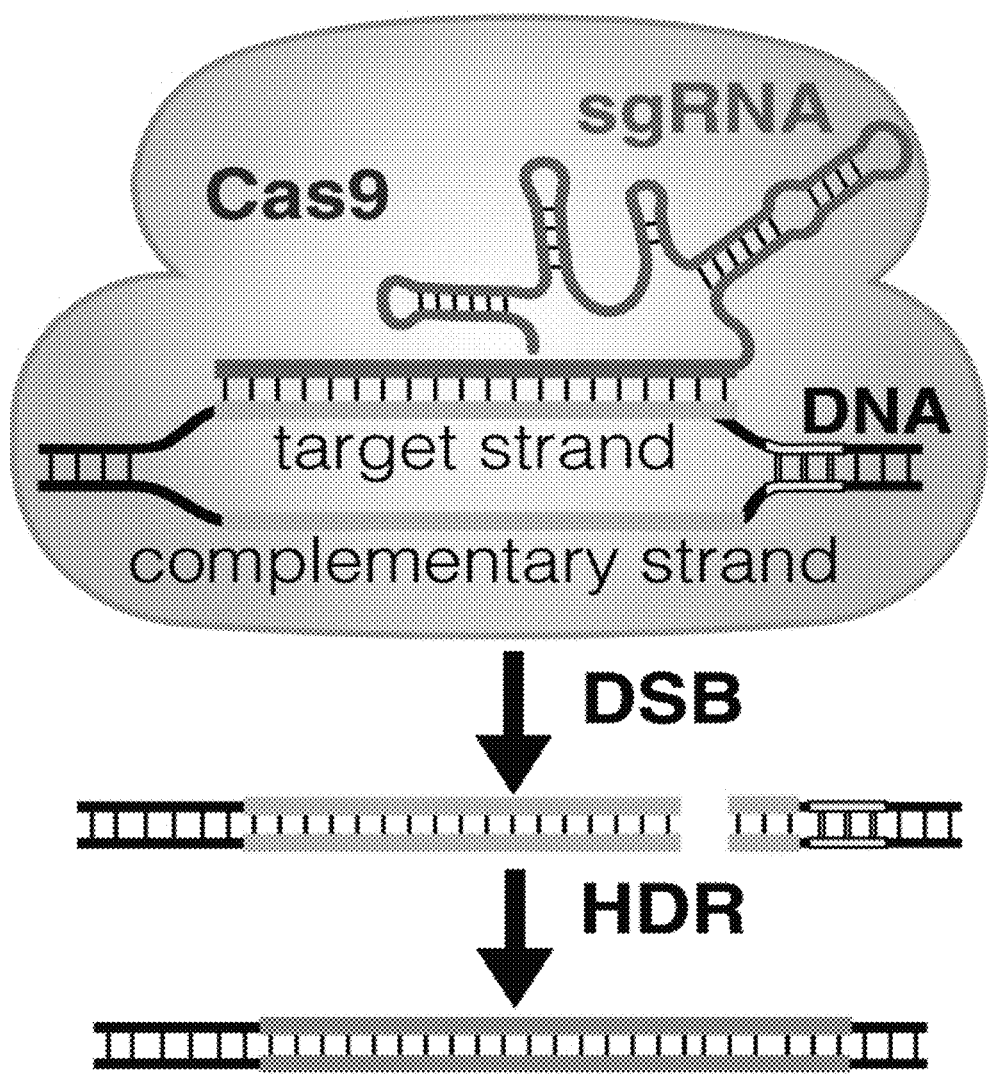
FIG. 1 shows an overview of Cas9-mediated genome editing. Heterologous expression of Cas9 from *Streptococcus pyogenes* (gray) and a chimeric sgRNA, containing a 80-bp scaffold sequence to facilitate Cas9 binding (in pink) and a 20-bp spacer identical to a region on the host chromosome (in blue) flanked by a 3' NGG PAM (in yellow) generates a DSB. In Archaea, HDR (in orange) is the prevalent mechanism for DSB repair and can be leveraged for genome editing by providing appropriate repair templates for targeted insertions, deletions, or allelic replacements.

The CRISPR (Clustered Regularly Interspaced Palindromic Repeats) array and associated cas genes are widespread in microbial genomes, where they confer acquired immunity to phage and foreign DNA elements. The type IIA system from *Streptococcus pyogenes* is especially well characterized and has been widely applied as a remarkably effective genome editing tool. During genome editing, heterologous expression of a RNA-guided DNA endonuclease and a chimeric single guide (sg) RNA, comprised of a 20 bp spacer that targets the chromosome and a 80 bp scaffold that binds a RNA-guided DNA endonuclease, leads to a lethal double-strand break (DSB) at all target sites within the genome that are flanked by a 3' NGG protospacer adjacent motif (PAM) (FIG. 1). In eukaryotes, the non-homologous end joining (NHEJ) repair pathway can mend the DSB by generating simple insertions or deletions at the sgRNA target site, thus preventing additional rounds of RNA-guided DNA endonuclease-mediated cleavage. Alternatively, the native homology-dependent repair (HDR) pathway can repair the fatal DSB, so long as a repair template that modifies or removes the sgRNA target site is provided, again preventing additional rounds of Cas9-mediated cleavage (FIG. 1). Appropriately designed repair templates allow recovery of strains with precise insertions and/or deletions, allowing unprecedented ability to manipulate the genomes of these diploid (or polyploid) organisms. While RNA-guided DNA endonuclease-mediated genome editing has been successfully and broadly implemented in eukaryotes, similar progress has not been achieved in prokaryotes, with Cas9-mediated genome editing having been demonstrated in only ten bacterial genera; to our knowledge, it has not been applied in archaea.

Archaea have been recognized as a phylogenetically distinct group since the 1990s and it is now well-established that they are prevalent in many environments, often providing keystone ecosystem functions. As a result, they play a major role in the biogeochemical cycling of nitrogen, sulfur and carbon. Methanogenic archaea are particularly noteworthy from this standpoint. These microorganisms are widely distributed in strictly anaerobic environments, such as waterlogged rice paddies, sewage treatment plants, and the digestive systems of numerous animals, where they generate the overwhelming majority of methane released in the atmosphere. As such, it is not surprising that they have a significant impact on climate change and the global carbon cycle. Members of the genus *Methanosarcina* are among the most abundant and metabolically versatile methanogens known. They are also genetically tractable and have emerged as important model organisms for genetic analysis of methanogen biology. While the range of genetic techniques available for use in *Methanosarcina* is fairly comprehensive, slow-growth and fastidious cultivation requirements have dramatically affected the pace of genetic studies within this genus.

Provided herein are RNA-guided DNA endonuclease-mediated editing techniques driven by native HDR machinery in Archaea that is extremely rapid and efficient, even when multiple mutations are simultaneously introduced. Furthermore, methods of co-expression of Archaea NHEJ machinery along with a RNA-guided DNA endonuclease-sgRNA complex allows for robust template-independent repair.

Methods and compositions now will be described more fully hereinafter with reference to the accompanying drawings, in which some, but not all embodiments of the methods and compositions are shown. Indeed, the methods and compositions can be embodied in many different forms and should not be construed as limited to the embodiments set forth herein; rather, these embodiments are provided so that this disclosure will satisfy applicable legal requirements.

Likewise, many modifications and other embodiments of the methods and compositions described herein will come to mind to one of skill in the art to which the methods and compositions pertain having the benefit of the teachings presented in the foregoing descriptions and the associated drawings. Therefore, it is to be understood that the methods and compositions are not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the systems and methods pertain.

As used herein, the term "and/or" includes any and all combinations of one or more of the associated listed items. As used herein, the singular forms "a," "an," and "the" are intended to include the plural forms as well as the singular forms, unless the context clearly indicates otherwise.

The embodiments illustratively described herein suitably can be practiced in the absence of any element or elements, limitation or limitations that are not specifically disclosed herein. Thus, for example, in each instance herein any of the terms "comprising," "consisting essentially of," and "consisting of" may be replaced with either of the other two terms, while retaining their ordinary meanings.

The term "about" in association with a numerical value means that the numerical value can vary plus or minus by 5% or less of the numerical value. All patents, patent applications, and other scientific or technical writings referred to anywhere herein are incorporated by reference herein in their entirety.

Archaea

Archaea are a domain of single-celled microorganisms having unique properties that distinguish them from Bacteria and Eukarya. The Euryachaeota and TACK are two phyla of Archaea. Euryarchaeota include methanogens, which produce methane, and halobacteria, which can survive at extreme concentrations of salt, and additionally some extremely thermophilic aerobes and anaerobes.

Methanogens are microorganisms that produce methane as a metabolic byproduct in anoxic/hypoxic conditions. Methanogens include, for example, *Methanobacterium bryantii, Methanobacterium formicum, Methanobrevibacter arboriphilicus, Methanobrevibacter gottschalkii, Methanobrevibacter ruminantium, Methanobrevibacter smithii, Methanococcus chunghsingensis, Methanococcus burtonii, Methanococcus aeolicus, Methanococcus deltae, Methanococcus jannaschii, Methanococcus maripaludis, Methanococcus vannielii, Methanocorpusculum labreanum, Methanoculleus bourgensis* (*Methanogenium olentangyi & Methanogenium bourgense*), *Methanoculleus marisnigri, Methanoflorens stordalenmirensis, Methanofollis liminatans, Methanogenium cariaci, Methanogenium frigidum, Methanogenium organophilum, Methanogenium wolfei, Methanomicrobium mobile, Methanopyrus kandleri, Methanoregula boonei, Methanosaeta concilii, Methanosaeta thermophile, Methanosarcina acetivorans, Methanosarcina barkeri, Methanosarcina mazei, Methanosphaera stadtmanae, Methanospirillium hungatei, Methanothermobacter defluvii* (*Methanobacterium defluvii*), *Methanothermobacter thermautotrophicus* (*Methanobacterium thermoautotrophicum*), *Methanothermobacter thermoflexus* (*Methanobacterium thermoflexum*), *Methanothermobacter wolfei* (*Methanobacterium wolfei*), and *Methanothrix sochngenii*.

Haloarchaea are a class of the Euryarchaeota and are found in water saturated or nearly saturated with salt. Examples include *Haladaptatus* sp., *Haladaptatus* sp., *Halalkalicoccus* sp., *Halanaeroarchaeum* sp., *Halapricum* sp., *Halarchaeum* sp., *Haloarchaeobius* sp., *Haloarcula* sp., *Halobacterium* sp., *Halobaculum* sp., *Halobellus* sp., *Halobiforma* sp., *Halocalculus* sp., *Halococcus* sp., *Halococcus agarilyticus* sp., *Haloferax* sp., *Halogeometricum* sp., *Halogranum* sp., *Halohasta* sp., *Halolamina* sp., *Halomarina* sp., *Halomicroarcula* sp., *Halomicrobium* sp., *Halonotius* sp., *Haloparvum* sp., *Halopelagius* sp., *Halopenitus* sp., *Halopiger* sp., *Haloplanus* sp., *Haloquadratum* sp. *Haloquadratum* sp., *Halorhabdus* sp., *Halorientalis* sp., *Halorubellus* sp., *Halorubrum* sp., *Halorussus* sp., *Halosiccatus* sp., *Halosimplex* sp., *Halostagnicola* sp., *Halostella* sp., *Haloterrigena* sp., *Halovarius* sp., *Halovenus* sp., *Halovivax* sp., *Natrialba* sp., *Natribaculum* sp., *Natrinema* sp., *Natronoarchaeum* sp., *Natronobacterium* sp., *Natronococcus* sp., *Natronolimnobius* sp., *Natronomonas* sp., *Natronorubrum* sp., *Salarchaeum* sp., *Salinarchaeum* sp., *Salinigranum* sp., *Salinigranum* sp., and *Salinirubrum* sp.

The TACK superphylum includes the Thaumarchaeota, Aigarchaeota, Crenarchaeota, and Korarchaeota.

Genetic Engineering Cassettes

Targeted genome engineering is genetic engineering where nucleic acid molecules are inserted, deleted, modified, modulated, or replaced in the genome of a living organism or cell. Targeted genome engineering can involve substituting nucleic acids, integrating nucleic acids into, or deleting nucleic acids from genomic DNA at a target site of interest to manipulate (e.g., increase, decrease, knockout, activate, interfere with) the expression of one or more genes. General methods of genetic engineering in Archaea are described in, for example, Allers & Mevarech, Archaeal Genetics—The Third Way, Nature Reviews Genetics, 6:58 (2005) and Leigh et al., Model Organisms for Genetics in the Domain Archaea: methanogens, Halophiles, Thermococcales, and Sulfolobales, FEMS Microbiol. Rev. 35:577 (2011). The genetic tool described in these references are incorporated by reference herein in their entirety.

A genetic engineering cassette can comprising a first Archaea or Euyarchaeota promoter operably linked to one or more sgRNA sequences (e.g., 1, 2, 3, 4, 5, 10 or more), a homologous recombination editing template comprising two homology arms with a deletion portion, a substitution portion, or an insertion portion between the two homology arms, wherein the two homology arms have homology to a Archaea or Euyarchaeota nucleic acid molecule. Where more than one sgRNA sequence is present, the two or more sgRNA sequences can be separated by 5, 10, 20, 30, 50, 100 or more base pairs of a nucleic acid linker.

The promoter can be an inducible promoter. An inducible promoter is active under specific circumstances. An inducible promoter can be positively inducible. That is, in the inactive state, the promoter is inactive because an activator protein cannot bind the promoter. After an inducer binds to the activator protein, the activator protein can bind to the promoter, turning it on (i.e., active state) and initiating transcription. An inducible promoter can be negatively inducible. That is, in the inactive state, the promoter is inactive because a bound repressor protein actively prevents transcription. Once an inducer binds the repressor protein, the repressor protein is removed from the DNA. With the repressor protein absent, transcription is turned on (i.e., active state). Inducible promoters can be, for example, chemically inducible promoters, temperature inducible promoters, or light inducible promoters. In an inactive state an inducible promoter initiates transcription at a rate that is about 30, 40, 50, 60, 70, 80, 90, 95, 99 or 100 percent less than when the promoter is an active state.

Archaea or Euyarchaeota promoters are known in the art and include, for example, bop promoter, fdx promoter, gdh promoter, csg promoter, PhmtB promoter, ParaS promoter, and malE promoter. Leigh et al., Model Organisms for Genetics in the Domain Archaea: methanogens, Halophiles, Thermococcales, and Sulfolobales, FEMS Microbiol. Rev. 35:577 (2011).

An Archaea or Euyarchaeota inducible promoter can be an inducible methanogen or halobacteria promoter. Such promoters include, for example, tnaA tryptophan inducible promoter of *Haloferax volcanii* (Large et al., Mol. Microbiol. 66:1092 (2007)), the nitrogen inducible promoter nif of *Methanococcus maripaludis* (Lie and Leigh, J. Bacteriol. 184:5301 (2002)), the tetracycline inducible mcr promoters of *Methanosarcina acetivorans* and *Methanosarcina barkeri* (Guss et al., Archaea, 2:193 (2008), and the fbp (TK2164) promoter of *Thermococcus kodakerensis* (Kanai et al., J. Biol. Chem. 282:33659 (2007)).

The Archaea or Euyarchaeota nucleic acid molecule can be a methanogen or halobacteria nucleic acid molecule.

The deletion portion, the substitution portion, or the insertion portion between the two homology arms can further comprises a restriction endonuclease site.

A genetic engineering cassette can be present in a vector, wherein the vector further comprises a nucleic acid molecule encoding an RNA-guided DNA endonuclease protein operably linked to a second Archaea or Euyarchaeota promoter, such as a methanogen or halobacteria promoter. The promoter can be an inducible promoter. In an embodiment the nucleic acid molecule encoding an RNA-guided DNA endonuclease protein operably linked to a second Archaea or Euyarchaeota promoter is present in the genetic engineering cassette.

A vector can further comprise an Archaea, Euyarchaeota, methanogen, or halobacteria origin of replication. An origin of replication can be helpful when removing the gene-editing machinery after mutant generation, that is, to generate a mutant that does not contain the foreign DNA introduced for the purposes of gene editing.

A vector can further comprise a selection marker, a counter-selection marker, or both a selection marker and a counter-selection marker.

Vectors described herein can be used in, for example, methods of homology directed repair-assisted engineering in Archaea, Euyarchaeota, methanogens, or halobacteria. The methods can comprise delivering one or more of the vectors to Archaea, Euyarchaeota, methanogen, or halobacteria host cells. Transformed Archaea, Euyarchaeota, methanogen, or halobacteria host cells can be isolated.

Methods can further comprise curing the transformed Archaea, Euyarchaeota, methanogen, or halobacteria host cells of the one or more vectors, wherein the vectors comprise a counter-selectable marker, by subjecting the transformed Euyarchaeota host cells to a counter-selection technique. A counter-selectable marker can be used to remove plasmids containing the homologous repair template, the RNA-guided DNA endonuclease genes and sgRNA. Under appropriate growth conditions, a counter-selectable marker promotes the death of the microorganisms harboring it. Transformed host cells that have integrated a vector containing a counter-selectable marker, retain a copy of the counter-selectable marker in the chromosome and are eliminated in the presence of the counter-selective compound. Counter-selectable markers can therefore be used for the positive selection of mutants that have undergone defined genetic alterations leading to the loss of the marker. A counter-selectable marker can be, for example, (hpt) to facilitate curing of gene editing vector. This marker confers sensitivity to the purine analog 8-aza-2,6-diaminopurine (8ADP) in strains that are upp+ and lack the native hpt gene. See Atomi et al. Frontiers in Microbiol. Vol. 3, Art. 337 (2012). Other counter-selectable markers include, for example, pyrE, pyrF, which confer sensitivity to 5-fluoroorotic acid (5FOA).

A counter-selection technique means exposing the transformed host cell to the chemical to which the counter-selectable marker is sensitive.

In an embodiment the RNA-guided DNA endonuclease comprises a bacterial endonuclease such as a Cas 9 protein, such as *S. pyogenes* Cas 9.

In an embodiment a method for testing for gene essentiality is provided. One or more vectors of comprising a first Archaea, Euyarchaeota, methanogen, or halobacteria promoter operably linked to one or more sgRNA sequences (e.g., about 1, 2, 3, 4, 5, 6, 7, or more) that target a specific Archaea, Euyarchaeota, methanogen, or halobacteria gene, and a nucleic acid molecule encoding an RNA-guided DNA endonuclease protein operably linked to a second Archaea, Euyarchaeota, methanogen, or halobacteria promoter, to a first set of Archaea, Euyarchaeota, methanogen, or halobacteria host cells to generate a first set of transformed cells. The first and second promoters can be inducible promoters. A second set of transformed cells is prepared by delivering one or more vectors targeting the specific Archaea, Euyarchaeota, methanogen, or halobacteria gene comprising a third Archaea, Euyarchaeota, methanogen, or halobacteria promoter operably linked to one or more sgRNA sequences, a homologous recombination editing template comprising two homology arms with a deletion portion, a substitution portion, or an insertion portion between the two homology arms, wherein the two homology arms have homology to a Archaea, Euyarchaeota, methanogen, or halobacteria nucleic acid molecule, and a nucleic acid molecule encoding an RNA-guided DNA endonuclease protein operably linked to a fourth Archaea, Euyarchaeota, methanogen, or halobacteria promoter to a second set of Archaea, Euyarchaeota, methanogen, or halobacteria host cells. The third and fourth promoters can be inducible promoters.

The ratio of a number of cells in the first set of transformed cells to a number of cells in the second set of transformed cells is determined. If a gene is essential, then the number of transformed cells should be low in number (e.g., about 1, 5, 10, 20, or 50 cells) for both the first and second set of transformed cells. A ratio of first set of transformed cells to a number of cells in the second set of transformed cells is therefore about 1:1, 1:2, or 2:1. If a gene is non-essential, then in the presence of a repair template transformed cell should be present in large numbers (the second set of transformed cells), while only a few transformed cells should be present in the first set of transformed cells. The large number of cells can be about 500, 1,000, 2,000, 3,000 or more. The few transformed cells can be about 1, 5, 10, 20, or 50 cells. A ratio of first set of transformed cells to a number of cells in the second set of transformed cells is therefore about 1:300, 1:400, 1:500, 1:600 or 1:700.

In an embodiment methods of non-homologous end joining ("NHEJ") in bacteria, eukaryotic cells, Archaea cells is provided. NHEJ repairs double-strand breaks in DNA. NHEJ is considered "non-homologous" because the broken ends are directly ligated without the need for a homologous template. This is different from homology directed repair, which requires a homologous sequence to guide repair. NHEJ typically utilizes short homologous DNA sequences called microhomologies to guide repair. Microhomologies can be present in single-stranded overhangs of double-strand breaks. Where the overhangs are compatible, NHEJ can repair the break accurately.

Methods are provided that rely upon NHEJ. In an embodiment, a vector comprises a NHEJ genetic engineering cassette comprising nucleic acid molecules encoding a methanogen DNA ligase, a methanogen polymerase, a methanogen phosphoesterase, and a methanogen Ku protein. The nucleic acid molecules can be operably linked to one or more methanogen promoters, which can be inducible promoters. Each or the four nucleic acid molecules can have its own individual promoter. The nucleic acid molecules can be present as an operon, wherein the operon is operably linked to a first methanogen promoter, which can be inducible. An operon is functioning unit of DNA containing a cluster of genes or expression coding sequences under the control of a single promoter. The vector additionally comprises a second methanogen promoter operably linked to one or more sgRNA sequences and a third methanogen promoter operably linked to a nucleic acid molecule encoding a RNA-guided DNA endonuclease protein.

In an embodiment, a methanogen DNA ligase, a methanogen polymerase, a methanogen phosphoesterase, and a methanogen Ku protein are from *Methanocella paludicola* SANAE. These have the following locus tags: Ku protein (MCP_0581), Ligase (MCP_2126), Pol (MCP_2125), PE (MCP_2127). Additionally Ku proteins from the following organisms can be used: *Methanobacterium paludis* strain SWAN1 (CP002772), *Methanobacterium* sp. MB1 (HG425166.1), *Methanobacterium lacus* strain AL-21 (CP002551.1), *Methanobacterium subterraneum* strain A8p (CP017768.1), *Methanobacterium* sp. MZA1 (CP017767.1), *Methanobacterium* sp. BAmetb5 (CP022706.1), *Methanobacterium formicicum* strain BRM9 (CP006933.1), *Methanobacterium formicicum* DSM1535 (LN515531.1), *Methanobacterium formicicum* Mb9 (LN734822.1), and *Methanobacterium* sp. MO-MB1 (CP017766.1).

LigD of *Methanocella arvoryzae* (MCP_2125) can be used as a ligase. Pol of *Methanocella arvoryzae* (MCP_2125) can be used as a polymerase. PE of *Methanocella arvoryzae* (MCP_2125) can be used as a phosphoesterase.

An embodiment comprises a method of deleting all or part of a nucleic acid molecule in a methanogen host cell or a bacteria host cell comprising delivering one or more NHEJ vectors described herein to methanogen or bacterial host cells, and isolating transformed methanogen host cells or transformed bacterial host cells. The gene editing frequency can be about 10, 20, 30, 40, 50, 60% or higher. A nucleic acid deletion can be about 25, 50, 75, 100, 500, 1,000, 2,000, 3,000, or more nucleotides long.

Polynucleotides

The terms "polynucleotide," "nucleotides," "nucleic acid molecule" and "oligonucleotide" are used interchangeably. They refer to a polymeric form of nucleotides of any length, either deoxyribonucleotides or ribonucleotides, or analogs thereof. Polynucleotides can have any three dimensional structure, and can perform any function, known or unknown. Nucleic acid molecule means a single- or double-stranded linear polynucleotide containing either deoxyribonucleotides or ribonucleotides that are linked by 3'-5'-phosphodiester bonds. A nucleic acid construct is a nucleic acid molecule that is isolated from a naturally occurring gene or that has been modified to contain segments of nucleic acids that are combined and juxtaposed in a manner that would not otherwise exist in nature. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), single guide RNA (sgRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide can comprise one or more modified nucleotides, such as methylated nucleotides and nucleotide analogs. If present, modifications to the nucleotide structure can be imparted before or after assembly of the polymer. The sequence of nucleotides can be interrupted by non-nucleotide components. A polynucleotide can be further modified after polymerization, such as by conjugation with a labeling component.

A recombinant nucleic acid molecule, for instance a recombinant DNA molecule, is a nucleic acid molecule formed in vitro through the ligation of two or more nonhomologous DNA molecules (for example a recombinant plasmid containing one or more inserts of foreign DNA cloned into at least one cloning site).

A gene is any polynucleotide molecule that encodes a polypeptide, protein, or fragments thereof, optionally including one or more regulatory elements preceding (5' non-coding sequences) and following (3' non-coding sequences) the coding sequence. In one embodiment, a gene does not include regulatory elements preceding and following the coding sequence. A native or wild-type gene refers to a gene as found in nature, optionally with its own regulatory elements preceding and following the coding sequence. A chimeric or recombinant gene refers to any gene that is not a native or wild-type gene, optionally comprising regulatory elements preceding and following the coding sequence, wherein the coding sequences and/or the regulatory elements, in whole or in part, are not found together in nature. Thus, a chimeric gene or recombinant gene comprise regulatory elements and coding sequences that are derived from different sources, or regulatory elements and coding sequences that are derived from the same source, but arranged differently than is found in nature. A gene can encompass full-length gene sequences (e.g., as found in nature and/or a gene sequence encoding a full-length polypeptide or protein) and can also encompass partial gene sequences (e.g., a fragment of the gene sequence found in nature and/or a gene sequence encoding a protein or fragment of a polypeptide or protein). A gene can include modified gene sequences (e.g., modified as compared to the sequence found in nature). Thus, a gene is not limited to the natural or full-length gene sequence found in nature.

Polynucleotides can be purified free of other components, such as proteins, lipids and other polynucleotides. For example, the polynucleotide can be 50%, 75%, 90%, 95%, 96%, 97%, 98%, 99%, or 100% purified. A polynucleotide existing among hundreds to millions of other polynucleotide molecules within, for example, cDNA or genomic libraries, or gel slices containing a genomic DNA restriction digest are not to be considered a purified polynucleotide.

Polynucleotides can comprise additional heterologous nucleotides that do not naturally occur contiguously with the polynucleotides. As used herein the term "heterologous" refers to a combination of elements that are not naturally occurring or that are obtained from different sources.

Degenerate polynucleotide sequences encoding polypeptides described herein, as well as homologous nucleotide sequences that are at least about 80, or about 85, 90, 91, 92, 93, 94, 95, 96, 97, 98, or 99% identical to polynucleotides described herein and the complements thereof are also polynucleotides. Degenerate nucleotide sequences are polynucleotides that encode a polypeptide described herein or fragments thereof, but differ in nucleic acid sequence from the wild-type polynucleotide sequence, due to the degeneracy of the genetic code. Complementary DNA (cDNA) molecules, species homologs, and variants of polynucleotides that encode biologically functional polypeptides also are polynucleotides.

Polynucleotides can be obtained from nucleic acid sequences present in, for example, a microorganism such as a yeast or bacterium. Polynucleotides can also be synthesized in the laboratory, for example, using an automatic synthesizer. An amplification method such as PCR can be used to amplify polynucleotides from either genomic DNA or cDNA encoding the polypeptides.

Polynucleotides can comprise coding sequences for naturally occurring polypeptides or can encode altered sequences that do not occur in nature.

Unless otherwise indicated, the term polynucleotide or gene includes reference to the specified sequence as well as the complementary sequence thereof.

The expression products of genes or polynucleotides are often proteins, or polypeptides, but in non-protein coding genes such as rRNA genes or tRNA genes, the product is a functional RNA. The process of gene expression is used by all known life forms, i.e., eukaryotes (including multicellular organisms), prokaryotes (bacteria and archaea), and viruses, to generate the macromolecular machinery for life. Several steps in the gene expression process can be modulated, including the transcription, up-regulation, RNA splicing, translation, and post-translational modification of a protein.

Homology refers to the similarity between two nucleic acid sequences. Homology among DNA, RNA, or proteins is typically inferred from their nucleotide or amino acid sequence similarity. Significant similarity is strong evidence that two sequences are related by evolutionary changes from a common ancestral sequence. Alignments of multiple sequences are used to indicate which regions of each sequence are homologous. The term "percent homology" is used herein to mean "sequence similarity." The percentage of identical nucleic acids or residues (percent identity) or the percentage of nucleic acids residues conserved with similar physicochemical properties (percent similarity), e.g. leucine and isoleucine, is used to quantify the homology.

Complement or complementary sequence means a sequence of nucleotides which forms a hydrogen-bonded duplex with another sequence of nucleotides according to Watson-Crick base-pairing rules. For example, the complementary base sequence for 5'-AAGGCT-3' is 3'-TTCCGA-5'. Downstream refers to a relative position in DNA or RNA and is the region towards the 3' end of a strand. Upstream means on the 5' side of any site in DNA or RNA.

As described herein, "sequence identity" is related to sequence homology. Homology comparisons can be conducted by eye or using sequence comparison programs. These commercially available computer programs can calculate percent (%) homology between two or more sequences and can also calculate the sequence identity shared by two or more amino acid or nucleic acid sequences. Sequence homologies may be generated by any of a number of computer programs known in the art, for example BLAST or FASTA.

Percentage (%) sequence identity can be calculated over contiguous sequences, i.e., one sequence is aligned with the other sequence and each amino acid or nucleotide in one sequence is directly compared with the corresponding amino acid or nucleotide in the other sequence, one residue at a time. This is called an "ungapped" alignment. Ungapped alignments are performed only over a relatively short number of residues. Although this is a very simple and consistent method, it fails to take into consideration that, for example, in an otherwise identical pair of sequences, one insertion or deletion can cause the following amino acid residues to be put out of alignment, thus potentially resulting in a large reduction in percent homology when a global alignment is performed. Therefore, most sequence comparison methods are designed to produce optimal alignments that take into consideration possible insertions and deletions without unduly penalizing the overall homology or identity score. This is achieved by inserting "gaps" in the sequence alignment to try to maximize local homology or identity.

CRISPR Systems

A Clustered Regularly Interspersed Short Palindromic Repeats/CRISPR-associated (CRISPR/Cas) system comprises components of a prokaryotic adaptive immune system that is functionally analogous to eukaryotic RNA interference, and that uses RNA base pairing to direct DNA or RNA cleavage. Directing DNA double stranded breaks requires an RNA-guided DNA endonuclease (e.g., Cas9 protein or the equivalent) and CRISPR RNA (crRNA) and tracer RNA (tracrRNA) sequences that aid in directing the RNA-guided DNA endonuclease/RNA complex to target nucleic acid sequence. The modification of a single targeting RNA can be sufficient to alter the nucleotide target of an RNA-guided DNA endonuclease protein. crRNA and tracrRNA can be engineered as a single cr/tracrRNA hybrid to direct the RNA-guided DNA endonuclease cleavage activity. A CRISPR/Cas system can be used in vivo in bacteria, yeast, fungi, plants, animals, mammals, humans, and in in vitro systems.

A CRISPR system can comprise transcripts and other elements involved in the expression of or directing the activity of CRISPR-associated ("Cas") genes, including sequences encoding an RNA-guided DNA endonuclease gene (i.e. Cas), a tracr (trans-activating CRISPR) sequence (e.g. tracrRNA or an active partial tracrRNA), a tracr-mate sequence (encompassing a "direct repeat" and a tracrRNA-processed partial direct repeat), a guide sequence, or other sequences and transcripts from a CRISPR locus. One or more elements of a CRISPR system can be derived from a type I, type II, type III, type IV, and type V CRISPR system. A CRISPR system comprises elements that promote the formation of a CRISPR complex at the site of a target sequence (also called a protospacer).

Typically, a CRISPR system can comprise a CRISPR complex (comprising a guide sequence hybridized to a target sequence and complexed with one or more RNA-guided DNA endonucleases) that results in cleavage of DNA in or near (e.g. within 1, 2, 3, 4, 5, 6, 7, 8, 9, 10, 20, 50, or more base pairs from) the target sequence.

The elements of CRISPR systems (e.g., direct repeats, homologous recombination editing templates, guide sequences, tracrRNA sequences, target sequences, priming sites, regulatory elements, and RNA-guided DNA endonucleases) are well known to those of skill in the art. That is, given a target sequence one of skill in the art can design functional CRISPR elements specific for a particular target sequence. The methods described herein are not limited to the use of specific CRISPR elements, but rather are intended to provide unique arrangements, compilations, and uses of the CRISPR elements.

Direct Repeats

A CRISPR direct repeat region contains sequences required for processing pre-crRNA into mature crRNA and tracrRNA binding. CRISPR direct repeat regions are about 23, 25, 28, 29, 30, 31, 32, 33, 34, 35, 36, 37, 40, 45, 50, 55 or more base pairs. Direct repeat regions can have dyad symmetry, which can result in the formation of a secondary structure such as a stem-loop ("hairpin") in the RNA. A genetic engineering cassette can comprise 2 or 3 CRISPR direct repeats, which can have the same or different sequence.

A genetic engineering cassette described herein can have direct repeats flanking a spacer region, wherein the spacer region comprises a homologous recombination template and a guide sequence. The most commonly used type II CRISPR/Cas9 direct repeats can be found in the following references: Jinek et al. A programmable dual-RNA-guided DNA endonuclease in adaptive bacterial immunity. Science. 337:816 (2012); Bao et al., ACS Synth Biol 4:585 (2015); Bao et al. Nat Biotechnol 36:505 (2018). Other direct repeats are described in, for example, Makarova et al., An updated evolutionary classification of CRISPR-Cas systems. Nat Rev Microbiol. 13:722 (2015). One of ordinary skill in the art can select appropriate direct repeat sequences.

Homologous Recombination Editing Template

A template that can be used for recombination into a targeted locus comprising a target sequence is an "editing template" or "homologous recombination editing template." Guide RNA is coupled with an RNA-guided DNA endonuclease (e.g. Cas9) to create a DNA double-stranded break near a genomic region to be edited. A homologous recombination editing template is used to introduce desired mutations (e.g. deletion of nucleic acids, substitution of nucleic acids, insertion of nucleic acids) into a cell's genome. The cell can repair the double-stranded break with homology directed repair (HDR) via homologous recombination (HR) mechanism. To design a homologous recombination template a guide RNA is selected so the double-stranded cut site is within about 5, 10, 15, 20, 30, 40, 50, 60, 70, 80, 90, 100, 150, 200, 250, 300, 400, 500, 1,000 or more base pairs from the targeted genomic region. The length of HR arms on both sides of the mutation is selected (e.g., about 20, 30, 40, 50, 60, 100, 200, 300, 400, 500 or more nucleic acids or about 500, 400, 300, 200, 100, 60, 50, 40, 30, 20 or less nucleic acids). A target genome, target gene or sequence, and PAM sequence is selected. Mutations to be made to the target sequence and/or the PAM sequence are incorporated into the homologous recombination editing template. More than one homologous recombination editing templates (e.g., 2, 3, 4, 5 or more) can be present in a genetic engineering cassette.

Homologous recombination editing templates used to create specific mutations or insert new elements into a target sequence require a certain amount of homology surrounding the target sequence that will be modified. In an embodiment each of the HR arms has about 70, 80, 90, 95, 99 or 100% homology to the target sequence.

RNA-guided DNA endonucleases can continue to cleave DNA once a double stranded break is introduced and repaired. As long as the gRNA target site/PAM site remains intact, the RNA-guided DNA endonuclease may keep cutting and repairing the DNA. A homologous recombination editing template can be designed to block further endonuclease targeting after the initial double stranded break is repaired. For example, the homologous recombination editing template can be designed to mutate the PAM sequence or the sequence that is targeted by the sgRNA.

A homologous recombination editing template repairs a cleaved target polynucleotide by homologous recombination such that the repair results in a mutation comprising an insertion, deletion, or substitution of one or more nucleotides of the target polynucleotide. The mutation can result in one or more (e.g., 1, 2, 3, 4, or more) amino acid changes in a protein expressed from a gene comprising the target sequence.

A homologous recombination editing template can be provided in a vector, or provided as a separate polynucleotide. A homologous recombination editing template is designed to serve as a template in homologous recombination, such as within or near a target sequence cleaved by an RNA-guided DNA endonuclease as a part of a CRISPR complex. A homologous recombination editing template polynucleotide can be about 50, 60, 70, 80, 85, 90, 100, 105, 110, 120, 130, 150, 160, 175, 200, 300, 400, 500, 750, 1,000, 1,250, 1,500, 1,750, 2,000, 2,250, 2,500, 2,750, 3,000 or more nucleotides in length. A homologous recombination editing template polynucleotide can be about 3,000, 2,750, 2,500, 2,250, 2,000, 1,750, 1,500, 1,250, 1,000, 750, 500, 400, 300, 200, 175, 160, 150, 130, 120, 110, 105, 100, 90, 85, 80, 70, 60, 50 or less nucleotides in length. A homologous recombination editing template polynucleotide is complementary to a portion of a polynucleotide comprising the target sequence. When optimally aligned, an editing template polynucleotide will overlap with one or more nucleotides of a target sequence (e.g. about 1, 5, 10, 15, 20, 25, 30, 35, 40, 45, 50, 60, 70, 80, 90, 100 or more nucleotides).

In one embodiment, the methods provide for modification of a target polynucleotide in a host cell such as a eukaryotic cell, archaea cell, or a prokaryotic cell. In some embodiments, the method comprises allowing an RNA-guided DNA endonuclease complex to bind to the target polynucleotide to effect cleavage of the target polynucleotide thereby modifying the target polynucleotide, wherein the RNA-guided DNA endonuclease comprises an RNA-guided DNA endonuclease complexed with a guide sequence hybridized to a target sequence within the target polynucleotide.

A homologous recombination editing template provides for the specific modification of a target polynucleotide. A deletion portion of a homologous recombination editing template comprises nucleotides that direct the deletion of about 1, 2, 3, 4, 5, 6, 7, 8, 9, 10, 50, 100, 200, 500, 1,000, 1,500, 2,000, 3,000 or more nucleic acids from a targeted gene or genome. A deletion of a certain amount of nucleic acids from a targeted gene can result in an inoperative gene product or no expression of the gene product. A gene deletion or knockout refers to a genetic technique in which a gene is made inoperative. That is, a gene product is no longer expressed. Knocking out two genes simultaneously results in a double knockout. Similarly, triple knockout (TKO) and quadruple knockouts (QKO) are used to describe three or four knocked out genes, respectively.

A substitution portion of a homologous recombination template comprises nucleotides that direct the substitution of about 1, 2, 3, 4, 5, 6, 7, 8, 9, 10, 20, 50, 100, 500, 1,000 or more nucleic acids with different nucleic acids in a targeted gene. A substitution of one or more nucleic acids in a targeted gene can result in the substitution of an amino acid (i.e., a different amino acid at a specific position) in protein expressed by the targeted gene.

An insertion portion of a homologous recombination template comprises nucleotides that direct the insertion of about 1, 2, 3, 4, 5, 6, 7, 8, 9, 10, 50, 100, 500, 1,000, 2,000, 3,000, 4,000 or more nucleic acids into a targeted gene. An insertion of a certain amount of nucleic acids into a targeted gene can result in an inoperative gene product, no expression of the gene product, or a gene product with new or additional biological functions.

Guide Sequences

As used herein, "single guide RNA," "guide RNA (gRNA)," "guide sequence" and "sgRNA" can be used interchangeably herein and refer to a single RNA species capable of directing RNA-guided DNA endonuclease mediated double stranded cleavage of target DNA. Single-stranded gRNA sequences are transcribed from double-stranded DNA sequences inside the cell.

A guide RNA is a specific RNA sequence that recognizes a target DNA region of interest and directs an RNA-guided DNA endonuclease there for editing. A gRNA has at least two regions. First, a CRISPR RNA (crRNA) or spacer sequence, which is a nucleotide sequence complementary to the target nucleic acid, and second a tracr RNA, which serves as a binding scaffold for the RNA-guided DNA endonuclease. The target sequence that is complementary to the guide sequence is known as the protospacer. The crRNA and tracr RNA can exist as one molecule or as two separate molecules, as they are in nature. gRNA and sgRNA as used herein refer to a single molecule comprising at least a crRNA region and a tracr RNA region or two separate molecules wherein the first comprises the crRNA region and the second comprises a tracr RNA region. The crRNA region of the gRNA is a customizable component that enables specificity in every CRISPR reaction. A guide RNA used in the systems and methods can also comprise an endoribonuclease recognition site (e.g., Csy4) for multiplex processing of gRNAs. If an endoribonuclease recognition site is introduced between neighboring gRNA sequences, more than one gRNA can be transcribed in a single expression cassette. Direct repeats can also serve as endoribonuclease recognition sites for multiplex processing.

A guide RNA used in the systems and methods described herein are short, single-stranded polynucleotide molecules about 20 nucleotides to about 300 nucleotides in length. The spacer sequence (targeting sequence) that hybridizes to a complementary region of the target DNA of interest can be about 14, 15, 16, 17, 18, 19, 20, 25, 30, 35 or more nucleotides in length.

A sgRNA capable of directing RNA-guided DNA endonuclease mediated substitution of, insertion at, or deletion of target sequence can be about 10, 11, 12, 13, 14, 15, 16, 17, 18, 19, 20, 30, 40, 50 or more nucleotides in length. A sgRNA capable of directing RNA-guided DNA endonuclease mediated substitution of, insertion at, or deletion of target sequence can be about 50, 40, 30, 20, 19, 18, 17, 16, 15, 14, 13, 12, 11 or less nucleotides in length. The sgRNA used to direct insertion, substitution, or deletion can include HR sequences for homology-directed repair.

sgRNAs can be synthetically generated or by making the sgRNA in vivo or in vitro, starting from a DNA template.

A sgRNA can target a regulatory element (e.g., a promoter, enhancer, or other regulatory element) in the target genome. A sgRNA can also target a protein coding sequence in the target genome.

Target Sequences

In the context of formation of a CRISPR complex, a target sequence or target nucleic acid molecule is a sequence to which a guide sequence is designed to have complementarity, where hybridization between a target sequence and a guide sequence promotes the formation of a CRISPR complex. Full complementarity is not necessarily required, provided there is sufficient complementarity to cause hybridization and promote formation of a CRISPR complex. A target sequence can comprise any polynucleotide, such as DNA or RNA polynucleotides. In some embodiments, a target sequence is located in the nucleus or cytoplasm of a cell. In some embodiments, the target sequence can be within an organelle of a eukaryotic cell, for example, mitochondrion or chloroplast.

The degree of complementarity between a guide sequence and its corresponding target sequence, when optimally aligned using a suitable alignment algorithm, is about 50%, 60%, 75%, 80%, 85%, 90%, 95%, 97.5%, 99% or more. Optimal alignment can be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies, ELAND (Illumina, San Diego, Calif.), SOAP (available at soap.genomics.org.cn), and Maq (available at maq.sourceforge.net).

The target polynucleotide of a CRISPR complex can be any polynucleotide endogenous or exogenous to a host cell, such as an Archaea cell, a eukaryotic cell, or a bacterial cell. For example, the target polynucleotide can be a polynucleotide residing in the nucleus of the host cell. The target polynucleotide can be a sequence coding a gene product (e.g., a protein) or a non-coding sequence (e.g., a regulatory polynucleotide). The target sequence can be associated with a PAM (protospacer adjacent motif); that is, a short sequence recognized by the CRISPR complex. The precise sequence and length requirements for the PAM differ depending on the RNA-guided DNA endonuclease used, but PAMs are typically 2-5 base pair sequences adjacent to the protospacer (that is, the target sequence). Those of ordinary skill in the art skilled can identify PAM sequences for use with a given RNA-guided DNA endonuclease enzyme.

TracrRNA Sequence

A tracrRNA sequence, which can comprise all or a portion of a wild-type tracrRNA sequence (e.g. about 20, 26, 32, 45, 48, 54, 63, 67, 85, or more nucleotides of a wild-type tracrRNA sequence), can also form part of a CRISPR complex. A tracrRNA sequence can hybridize along at least a portion of a tracrRNA sequence to all or a portion of a direct repeat sequence.

The degree of complementarity between a tracrRNA sequence and a tracr mate sequence along the length of the shorter of the two when optimally aligned is about 25%, 30%, 40%, 50%, 60%, 70%, 80%, 90%, 95%, 97.5%, 99%, or higher. In some embodiments, the tracrRNA sequence is about or more than about 5, 6, 7, 8, 9, 10, 11, 12, 13, 14, 15, 16, 17, 18, 19, 20, 25, 30, 40, 50, or more nucleotides in length.

Markers

One or more vectors that express sgRNA and/or RNA-guided DNA endonuclease proteins can further comprise a polynucleotide encoding for a marker protein, a selection marker protein, or a counter-selection marker protein.

A polynucleotide encoding a marker protein can be expressed on a separate vector from a vector that expresses sgRNA and/or RNA-guided DNA endonuclease proteins.

A marker protein is a protein encoded by a gene that when introduced into a cell confers a trait suitable for artificial selection. A marker can make a cell sensitive to a certain chemical. Marker proteins are used in laboratory, molecular biology, and genetic engineering applications to indicate the success of a transformation, a transfection or other procedure meant to introduce foreign nucleic acids into a cell. Marker proteins include, but are not limited to, fluorescent proteins and proteins that confer resistance to antibiotics, herbicides, or other compounds, which would be lethal to cells, organelles or tissues not expressing the resistance gene or allele. Examples of marker systems include gyrB mutants (novobiocin resistance), hmgR overexpression (mevinolin/simvastatin resistance), pac (puromycin resistance), APH3_I/II (neomycin resistance), thermostable hph mutants (hyromycin resistance), adh systems (butanol/benzyl alcohol resistance). See Atomi et al. Frontiers in Microbiol. Vol. 3, Art. 337 (2012). Other marker systems include positive selection for agmatine prototrophs in strains in which the argD gene, encoding arginine decarboxylase (pdaD), has been deleted; positive selection for uracil prototrophs in upp+ strains in which the pyrE and pyrF genes are deleted; positive selection for leucine prototrophs in strains in which the leuB gene is deleted; positive selection for tryptophan prototrophs in strains in which the trpE and trpAB genes are deleted; positive selection for histidine prototrophs in strains in which the hisA gene is deleted; positive selection for lactose prototrophs in strains in which the lacS gene is deleted. See id.

Selection of transformants is accomplished by growing the cells or tissues under selective pressure, i.e., on media containing the antibiotic, herbicide or other compound (e.g., novobiocin, mevinolin, simvastatin, puromycin, neomycin, hygromycinB, butanol/benzyl alcohol) or media lacking certain components (e.g. media lacking pyrimidines, leucine, tryptophan, or histidine) or media containing certain carbon sources (e.g., media containing lactose as the major carbon/energy source). If the marker protein is a "lethal" marker, cells which express the marker protein will live, while cells lacking the marker protein will die. If the marker protein is "non-lethal," transformants (i.e., cells expressing the selectable marker) will be identifiable by some means from non-transformants, but both transformants and non-transformants will live in the presence of the selection pressure.

Selective pressure refers to the influence exerted by some factor (such as an antibiotic, heat, light, pressure, or a marker protein) on natural selection to promote one group of organisms or cells over another. In the case of antibiotic resistance, applying antibiotics cause a selective pressure by killing susceptible cells, allowing antibiotic-resistant cells to survive and multiply.

Selective pressure can be applied by contacting the cells with an antibiotic and selecting the cells that survive. The antibiotic can be, for example, kanamycin, puromycin, spectinomycin, streptomycin, ampicillin, carbenicillin, bleomycin, erythromycin, polymyxin B, tetracycline, or chloramphenicol. Applying selective pressure to transformed cells is a selection and a counter-selection technique.

In an embodiment, the methods described herein can function without the use of a protein marker encoded by a genetic engineering cassette or by the vector.

Genetic Bar Codes

In an embodiment, a genetic engineering cassette or homologous recombination editing template, or guide sequence functions as a genetic barcode due to its unique sequence. The unique sequence can be used with next generation sequencing to quickly identify the mutation or mutations present in a transformed host cell. In an embodiment a genetic barcode is a unique sequence within a genetic engineering cassette that can be used in the same way. A genetic barcode can be present anywhere in the genetic engineering cassette, for example, between the homology arms.

RNA-Guided DNA Endonucleases

An RNA-guided DNA endonuclease protein is directed to a specific DNA target by a gRNA, where it causes a double-strand break. There are many versions of RNA-guided DNA endonucleases isolated from different organisms.

Each RNA-guided DNA endonuclease binds to its target sequence in the presence of a protospacer adjacent motif (PAM), on the non-targeted DNA strand. Therefore, the locations in a genome that can be targeted by different RNA-guided DNA endonuclease can be dictated by locations of PAM sequences. An RNA-guided DNA endonuclease cuts 3-4 nucleotides upstream of the PAM sequence. Recognition of the PAM sequence by an RNA-guided DNA endonuclease protein is thought to destabilize the adjacent DNA sequence, allowing interrogation of the sequence by the sgRNA, and allowing the sgRNA-DNA pairing when a matching sequence is present.

RNA-guided DNA endonucleases isolated from different bacterial species recognize different PAM sequences. For example, the SpCas9 nuclease cuts upstream of the PAM sequence 5'-NGG-3' (where "N" can be any nucleotide base), while the PAM sequence 5'-NNGRR(N)-3' is required for SaCas9 (from *Staphylococcus aureus*) to target a DNA region for editing. While the PAM sequence itself is necessary for cleavage, it is not included in the single guide RNA sequence.

RNA-guided DNA endonuclease proteins include, for example, Cas9 from *Streptococcus pyogenes* (SpCas9), *Neisseria meningitides* (NmCas9), *Streptococcus thermophiles* (St1Cas9), and *Staphylococcus aureus* (SaCas9) and Cpf1 from Lachnospiraceae bacterium ND2006 (LbCpf1) and Acidaminococcus sp. BV3L6 (AsCpf1).

Non-limiting examples of RNA-guided DNA endonuclease proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof. In some embodiments, the RNA-guided DNA endonuclease directs cleavage of both strands of target DNA within about 1, 2, 3, 4, 5, 6, 7, 8, 9, 10, 15, 20, 25, 50, 100, 200, 500, or more base pairs from the first or last nucleotide of a target sequence. In an embodiment a RNA-guided DNA endonuclease protein is type IIA or type IIB Cas protein.

In an embodiment, a coding sequence encoding an RNA-guided DNA endonuclease is codon optimized for expression in particular cells, such as Archaea cells, bacterial cells, or eukaryotic cells. The eukaryotic cells can be those of or derived from a particular organism, such as a yeast or a mammal, including but not limited to human, mouse, rat, rabbit, dog, or non-human primate. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence.

A system described herein can comprise one or more sgRNA molecules that are capable of binding a target nucleic acid and an RNA-guided DNA endonuclease protein that causes a double-stranded nucleic acid break of one or more additional target nucleic acid molecules. In this aspect, the genome can be cut at several different sites (e.g., 1, 2, 3, 4, 5, 6, 7, 8, 9, or 10 sites) at or near the same time, and the homology directed repair donor included in the genetic engineering cassette can be inserted into those one or more sites.

An RNA-guided DNA endonuclease can be expressed from a nucleic acid molecule that is present in a vector. A vector can comprise an RNA-guided DNA endonuclease and regulatory elements to be expressed by a transformed or transfected cell, whereby the RNA-guided DNA endonuclease and regulatory elements direct the cell to make RNA and protein. Different types of RNA-guided DNA endonucleases and regulatory elements can be transformed or transfected into different organisms including yeast, plants, bacteria, Archaea, and mammalian cells as long as the proper regulatory element sequences are used.

Once a target sequence and RNA-guided DNA endonuclease have been selected, the next step is to design specific guide RNA sequences. Several software tools exist for designing an optimal guide with minimum off-target effects and maximum on-target efficiency. Examples include Synthego Design Tool, Desktop Genetics, Benchling, and MIT CRISPR Designer.

In some embodiments, the RNA-guided DNA endonuclease is part of a fusion protein comprising one or more heterologous protein domains (e.g. about or more than about 1, 2, 3, 4, 5, 6, 7, 8, 9, 10, or more domains in addition to the RNA-guided DNA endonuclease). A CRISPR enzyme fusion protein can comprise any additional protein sequences, and optionally a linker sequence between any two domains. Examples of protein domains that may be fused to an RNA-guided DNA endonuclease include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-S-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP). An RNA-guided DNA endonuclease can be fused to a gene sequence encoding a protein or a fragment of a protein that bind DNA molecules or bind other cellular molecules, including but not limited to maltose binding protein (MBP), S-tag, Lex A DNA binding domain (DBD) fusions, GAL4 DNA binding domain fusions, and herpes simplex virus (HSV) BP16 protein fusions.

Vectors

In an embodiment, a vector comprises a genetic engineering cassette as described herein. Also provided herein are pools of vectors comprising two or more (e.g., 2, 5, 10, 50, 100, 1,000, 5,000, 10,000 or more) of the vectors described herein wherein each of the genetic engineering cassettes is unique.

A vector can comprise one or more insertion sites for nucleic acid molecules such as a genetic engineering cassette (e.g. about or more than about 1, 2, 3, 4, 5, 6, 7, 8, 9, 10, or more insertion sites), such as a restriction endonuclease recognition site.

Several aspects of the disclosure relate to vector systems comprising one or more vectors. Vectors can be designed for expression of RNA-guided DNA endonucleases, and polynucleotides (e.g. nucleic acid transcripts, proteins, or enzymes) in host cell such as Achaea, bacterial, or eukaryotic cells. For example, RNA-guided DNA endonucleases or polynucleotides can be expressed in insect cells (using baculovirus expression vectors), bacterial cells, yeast cells, or mammalian cells. Suitable cells are discussed further in Goeddel, GENE EXPRESSION TECHNOLOGY: METHODS IN ENZYMOLOGY 185, Academic Press, San Diego, Calif. (1990). Alternatively, a recombinant expression vector can be transcribed and translated in vitro, for example using T7 promoter regulatory sequences and T7 polymerase.

A vector or expression vector is a replicon, such as a plasmid, phage, or cosmid, to which another nucleic acid segment can be attached so as to bring about the replication of the attached segment. A vector is capable of transferring polynucleotides (e.g. gene sequences) to target cells.

Expression refers to the process by which a polynucleotide is transcribed from a nucleic acid template (such as into a sgRNA, tRNA or mRNA) and/or the process by which a transcribed mRNA is subsequently translated into peptides, polypeptides, or proteins. Transcripts and encoded polypeptides can be collectively referred to as "gene product."

Many suitable vectors and features thereof are known in the art. Vectors can contain, without limitation, a centromeric (CEN) sequence, an autonomous replication sequence (ARS), a promoter, an origin of replication, and a marker gene (e.g., auxotrophic, antibiotic, or other selectable markers). Examples of expression vectors include plasmids, yeast artificial chromosomes, 2µπι plasmids, yeast integrative plasmids, yeast replicative plasmids, shuttle vectors, episomal plasmids, and viral vectors. In an embodiment, the viral vector is a lentivirus vector, an adenovirus vector, or an adeno-associated vector (AAV).

Vectors can be introduced and propagated in a prokaryote. In some embodiments, a prokaryote is used to amplify copies of a vector to be introduced into a Archaea, bacterial, or eukaryotic cell or as an intermediate vector in the production of a vector to be introduced into a Archaea, bacterial, or eukaryotic cell (e.g. amplifying a plasmid as part of a viral vector packaging system). In some embodiments, a prokaryote is used to amplify copies of a vector and express one or more nucleic acids, such as to provide a source of one or more proteins for delivery to a host cell or host organism. Fusion vectors add a number of amino acids to a protein encoded therein, such as to the amino terminus of the recombinant protein. Such fusion vectors can serve one or more purposes, such as: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase.

Promoters and Other Regulatory Elements

Genetic engineering cassettes and vectors can comprise 1, 2, 3, 4, 5, or more promoters. The promoters can be the same or different promoters. A promoter is any nucleic acid sequence that regulates the initiation of transcription for a particular polypeptide-encoding nucleic acid under its control. A promoter minimally includes the genetic elements necessary for the initiation of transcription (e.g., RNA polymerase III-mediated transcription), and can further include one or more genetic regulatory elements that serve to specify the prerequisite conditions for transcriptional initiation. A promoter can be inducible or non-inducible A promoter can be a cis-acting DNA sequence, about 10, 20, 30, 40, 50, 60, 70, 80, 90, 100, 110, 120, or more base pairs long and located upstream of the initiation site of a gene, to which RNA polymerase can bind and initiate correct transcription. There can be associated additional transcription regulatory sequences that provide on/off regulation of transcription and/or which enhance (increase) expression of the downstream coding sequence. A coding sequence is the part of a gene or cDNA that codes for the amino acid sequence of a protein, or for a functional RNA such as a tRNA or rRNA.

A promoter can be encoded by an endogenous genome of a cell, or it can be introduced as part of a recombinantly engineered polynucleotide. A promoter sequence can be taken from one species and used to drive expression of a gene in a cell of a different species. A promoter sequence can also be artificially designed for a particular mode of expression in a particular species, through random mutation or rational design. In recombinant engineering applications, specific promoters are used to express a recombinant gene under a desired set of physiological or temporal conditions or to modulate the amount of expression of a recombinant nucleic acid.

Other regulatory elements include enhancers, internal ribosomal entry sites (IRES), and other expression control elements (e.g. transcription termination signals (i.e., terminators), such as polyadenylation signals and poly-U sequences). Vectors and genetic engineering cassettes described herein can additionally comprise one or more regulatory elements. Regulatory elements include those that direct constitutive expression of a nucleotide sequence in many types of host cell and those that direct expression of the nucleotide sequence only in certain host cells (e.g., tissue-specific regulatory sequences). Regulatory elements can also direct expression in a temporal-dependent manner, such as in a cell-cycle dependent or developmental stage-dependent manner, which may or may not also be tissue or cell-type specific.

Regulatory elements include enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981).

Two DNA sequences are operably linked if the nature of the linkage does not interfere with the ability of the sequences to affect their normal functions relative to each other. For instance, a promoter region would be operably linked to a coding sequence of a protein if the promoter were capable of effecting transcription of that coding sequence.

In an embodiment, a genetic engineering cassette does not comprise a promoter. Instead, one or more (e.g., about 1, 2, 3, 4, 5, or more) promoters are located on the vector at a position to act on the genetic engineering cassette (i.e., operably linked), which is placed into the vector.

A polynucleotide can also comprise a nucleotide sequence encoding a polypeptide linker sequence. Linkers are short (e.g., about 3 to 20 amino acids) polypeptide sequences that can be used to operably link protein domains. Linkers can comprise flexible amino acid residues (e.g., glycine or serine) to permit adjacent protein domains to move freely related to one another.

Delivery of Polynucleotides and Vectors to Host Cells

Methods are provided herein for delivering one or more polynucleotides, such as one or more vectors as described herein, one or more transcripts thereof, and/or one or more proteins transcribed therefrom, to a host cell. Also provided herein are cells produced by such methods, and organisms (such as animals, bacteria, Archaea, plants, or fungi) comprising or produced from such cells. Viral and non-viral based gene transfer methods can be used to introduce nucleic acids and vectors into host cells (e.g., eukaryotic cells, prokaryotic cells, Archaea, bacteria, yeast, fungi, mammalian cells, plant cells, or target tissues). Such methods can be used to administer nucleic acids encoding components of the systems described herein to cells in culture or in a host organism. Non-viral vector delivery systems include DNA plasmids, RNA (e.g. a transcript of a vector described herein), naked nucleic acid, and nucleic acid complexed with a delivery vehicle, such as a liposome. Viral vector delivery systems include DNA and RNA viruses, which can have either episomal or integrated genomes after delivery to the cell.

Methods of non-viral delivery of nucleic acids include lipofection, nucleofection, microinjection, biolistics, virosomes, liposomes, immunoliposomes, polycation or lipid: nucleic acid conjugates, naked DNA, artificial virions, and agent-enhanced uptake of DNA.

Viral vectors can be administered directly to host cells in vivo or they can be administered to cells in vitro, and the modified cells can optionally be administered to host organisms (ex vivo). Viral based vector systems include, for example retroviral, lentivirus, adenoviral, adeno-associated and herpes simplex virus vectors for gene transfer. Integration in the host genome is possible with retrovirus, lentivirus, and adeno-associated virus gene transfer methods, often resulting in long term expression of the inserted transgene. Additionally, high transduction efficiencies have been observed in many different cell types and target tissues.

Following insertion of a genetic expression cassette into an insertion site of a vector and upon expression in a host cell the guide sequence(s) direct(s) sequence-specific binding of a CRISPR complex to a target sequence in the host cell.

A genetic engineering cassette can be put into the insertion site of a vector comprising a first promoter upstream of the insertion site. Downstream of the insertion site the vector can comprise a terminator, a second promoter, a nucleic acid sequence encoding an RNA-guided DNA endonuclease protein.

An embodiment provides a pool of vectors comprising two or more (e.g., 2, 10, 50, 100, 200, 300, 400, 500, 1,000, 2,000, 3,000, 4,000, 5,000, 10,000, 15,000, 20,000, 25,000, 30,000 or more) of the vectors, wherein each of the genetic engineering cassettes is unique. Each genetic engineering cassette can be specific for (i.e. target) a different target nucleic acid. Several genetic engineering cassettes can be designed to target a single target sequence at several positions (e.g., about 2, 3, 4, 5, 10, 20, 50, 100, 1,000, or more) of the target sequence.

The following are provided for exemplification purposes only and are not intended to limit the scope of the invention described in broad terms above.

EXAMPLES

Example 1. Development of a Cas9-Dependent Genome Editing System for *Methanosarcina acetivorans*

Figure 2:
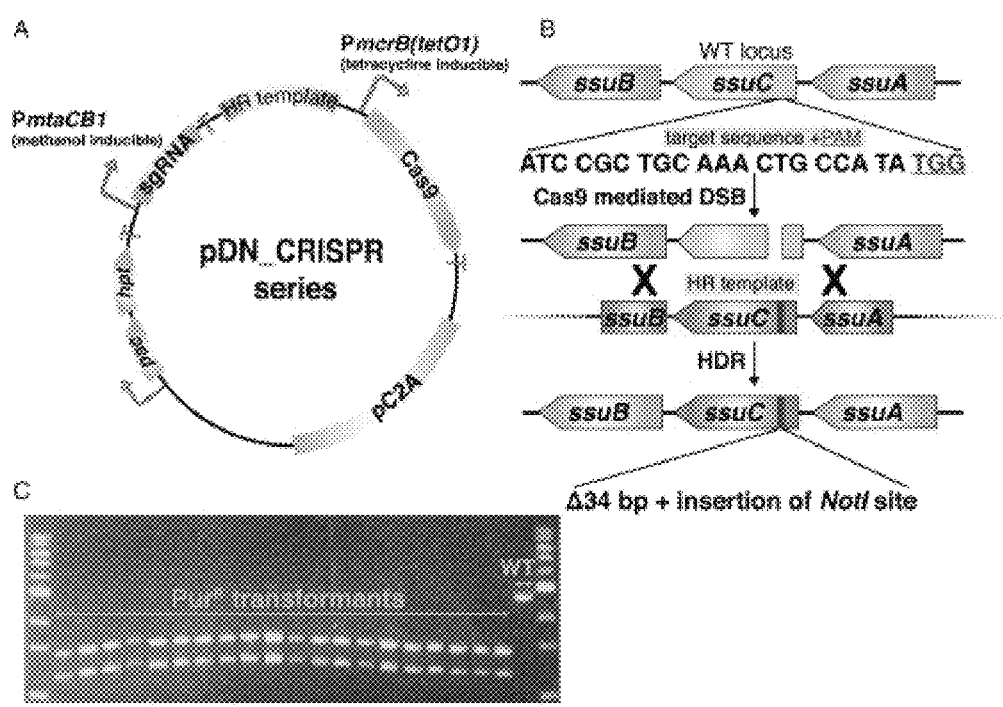
FIG. 2 shows Cas9-mediated genome editing in *M. acetivorans*. (A) Key elements of the pDN_CRISPR plasmid series include the Cas9 ORF from *S. pyogenes* fused to the tetracycline-inducible PmcrB(tetO1) promoter (in green), sgRNA(s) fused to the methanol-inducible PmtaCB1 promoter (in pink), a homology repair template (in orange), and the entire pC2A plasmid replicon containing an autonomous *Methanosarcina* origin of replication (in gray). The puromycin transacetylase (pac) marker enables selection of puromycin resistant ($Pur^R$) transformants and the hypoxanthine phosphoribosyltransferase (hpt) marker facilitates plasmid curing by counter-selection on medium containing 8ADP. Note: The *E. coli* replicon and resistance marker genes have not been shown. (B) Expression of sgRNA with a 20-bp target sequence (SEQ ID NO:39) identical to a region of the WT ssuC locus (in blue) flanked by a 3' NGG PAM (in red) with Cas9 generates a DSB at the ssuC locus. A region of the plasmid pDN211 contains a homology repair (HR) template to abolish the target site by generating a 34-bp deletion and simultaneously introducing a diagnostic NotI restriction endonuclease site in the ssuC ORF (in orange). (C) The chromosomal ssuC locus amplified from 20 $Pur^R$ transformants containing pDN211 as well as the parent strain (WWM60) and subjected to restriction digest with NotI. Upon digestion, 1.1-kbp and 1.3-kbp fragments are observed for all $Pur^R$ transformants (lanes 2-21), whereas a single 2.4-kbp fragment corresponding to the WT locus is observed for WWM60 (lane 22).

To determine whether the appropriate components for genome editing from *S. pyogenes* are functional in *M.* acetivorans, a Methanosarcina/E. coli shuttle vector was constructed that expresses the *S. pyogenes* Cas9 ORF from a tetracycline inducible *Methanosarcina* promoter (FIG. 2A). A derivative of this plasmid was also constructed that employs a methanol-inducible promoter to express an sgRNA that targets Cas9 to ssuC, a gene required for uptake of the methanogenesis inhibitor bromoethane sulfonic acid (BES) (Guss A M, Mukhopadhyay B, Zhang J K, Metcalf W W (2005) Genetic analysis of mch mutants in two *Methanosarcina* species demonstrates multiple roles for the methanopterin-dependent C-1 oxidation/reduction pathway and differences in $H_2$ metabolism between closely related species. *Mol Microbiol* 55(6):1671-1680) (FIGS. 2A & 2B). *M. acetivorans* was readily transformed with the Cas9-only plasmid pDN206 (78900±9940 $Pur^R$ transformants); however, pDN208, which contains the ssuC-targeting sgRNA in addition to Cas9, produced only 4±3 $Pur^R$ transformants. This difference in plating efficiency of more than four orders of magnitude strongly suggests that Cas9 is not toxic by itself, but that the Cas9-sgRNA complex from *S. pyogenes* is capable of generating a lethal DSB in *M. acetivorans*. Similar results were obtained with and without the inducers methanol and tetracycline.

Next, the ability of the native HDR machinery in *M. acetivorans* to repair the lethal DSB generated by the sgRNA-Cas9 complex was determined. To this end, repair templates of varying size were added to the ssuC-targeting vector. These repair templates generate a 34 bp deletion/frameshift mutation within ssuC that removes the targeting site while simultaneously introducing a diagnostic NotI restriction endonuclease site (FIG. 2B). Addition of repair templates with 1 kb homology arms to the plasmids relieved the lethal effect of targeting Cas9 to ssuC, generating nearly 20,000 $Pur^R$ transformants per 2 µg DNA. A similar plasmid with 0.5 kbp homology arms generated roughly half as many transformants. Significantly, the $10^3$-fold higher transformation efficiency for pDN211 relative to pDN208 indicated that 99.9% of the $Pur^R$ transformants are likely to be mutants, i.e. only 1 out of every 1000 $Pur^R$ transformants would still contain the WT locus. To validate this hypothesis, twenty of these transformants were genotyped by a performing a NotI digest of a PCR amplicon containing the edited ssuC locus: all tested positive for the introduced mutation (FIG. 2C). Further, as expected for null mutations in the ssu locus, all twenty transformants were resistant to 0.4 mM BES, a concentration lethal to the parent strain. Genome editing was also observed when plasmids were integrated into the chromosome using a φC31 integrase system. Guss A M, Rother M, Zhang J K, Kulkarni G, Metcalf W W (2008) New methods for tightly regulated gene expression and highly efficient chromosomal integration of cloned genes for *Methanosarcina* species. *Archaea* 2(3): 193-203.

Figure 3:
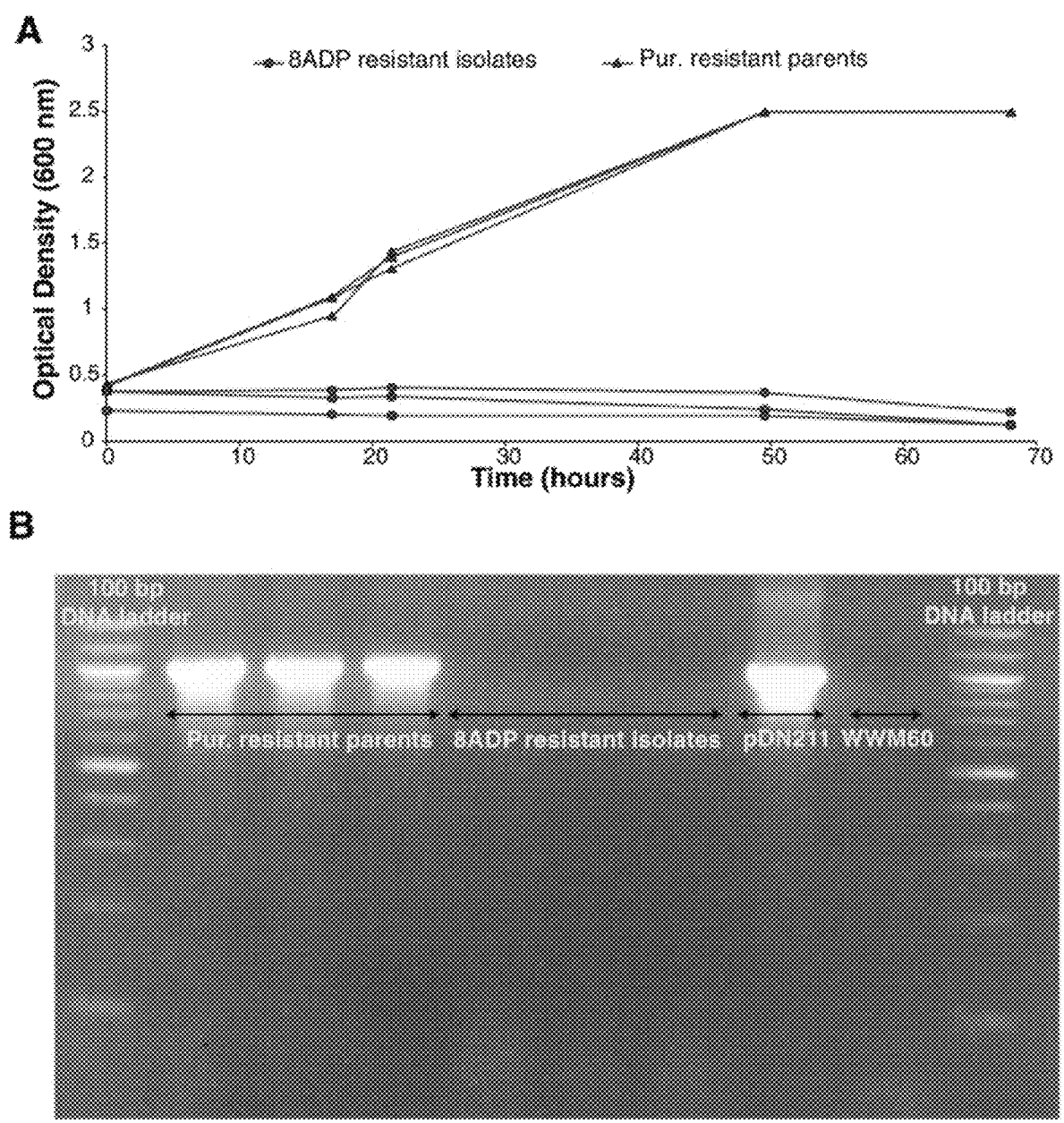
FIG. 3 shows use of the counter-selectable hpt marker to cure plasmids containing the genome editing machinery. (A) Growth curves for three independent puromycin-resistant ($Pur^R$) transformants (blue) and an $8ADP^R$ isolate derived from each PurR parent (red) in liquid medium containing TMA hydrochloride as the growth substrate and 2 µg/mL puromycin. $Pur^R$ transformants contain pDN211 in the WWM60 strain background. A 1:10 dilution of stationary-phase cultures grown in liquid medium containing TMA as the growth substrate was inoculated for growth measurement. (B) Primers to amplify the repA gene in pC2A (approximately 1 kbp) were used to screen for the presence of the plasmid containing the genome editing machinery in each of the three $Pur^R$ parents (lanes 2-4) and $8ADP^R$ isolates (lanes 5-7). The plasmid pDN211 was used as a positive control (lane 8) and the parent strain WWM60 was used as a negative control (lane 9).

The initial gene-edited strains produced in these experiments retain the targeting machinery, thus, plasmid derivatives were constructed that include a counter-selectable marker (hpt) to facilitate curing of gene editing vector. This marker confers sensitivity to the purine analog 8-aza-2,6-diaminopurine (8ADP) in strains that lack the native hpt gene. Pritchett M A, Zhang J K, Metcalf W W (2004) Development of a markerless genetic exchange method for *Methanosarcina acetivorans* C2A and its use in construction of new genetic tools for methanogenic archaea. *Appl Environ Microbiol* 70(3):1425-1433. To validate the plasmid curing system, which has not previously been attempted in *Methanosarcina*, $8ADP^R$ clones were selected from three independent $Pur^R$ transformants constructed using the counter-selectable vectors. All $8ADP^R$ isolates analyzed were $Pur^S$ and also contain the frameshift mutation at the ssuC locus (FIG. 3A). PCR-based screening with plasmid-specific primers showed that the vector was indeed cured from these strains (FIG. 3B). These proof-of-principle experiments show that a Cas9-mediated genome editing technique can be used to effectively introduce unmarked mutations in *M. acetivorans*.

Example 2. Optimization of the Cas9-Dependent Genome Editing Technique in *M. acetivorans*

Figure 4:
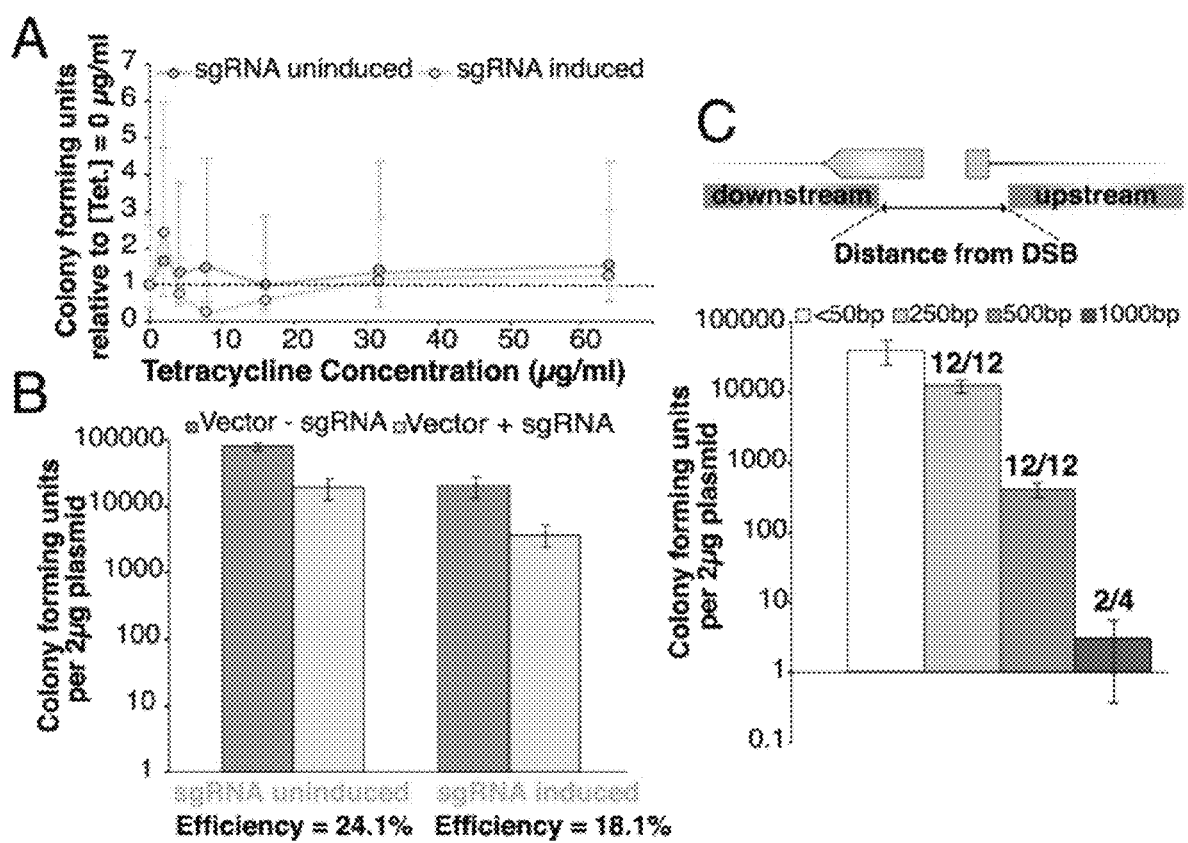
FIG. 4 shows optimization of Cas9-mediated genome editing in *M. acetivorans*. (A) A dose-response curve showing the relative transformation efficiency of pDN211 for different expression levels of Cas9 and the sgRNA. Transformants were plated on solid medium containing either TMA hydrochloride (sgRNA uninduced; in blue) or methanol (sgRNA induced; in green) as the growth substrate with tetracycline concentrations ranging from 0 to 64 µg/mL, as indicated. (B) Mean transformation efficiencies of pDN211 and pDN207 (a control vector that lacks the sgRNA targeting ssuC). (C) Mean transformation efficiencies of plasmids containing repair templates placed at variable distance from the sgRNA-directed DSB for ssuC. Values above each column represent the fraction of transformants for the corresponding plasmid that tested positive for the desired mutation by a PCR-based screen. The error bars represent one SD of the mean transformation efficiency for three independent transformation reactions. All transformations were plated on medium lacking tetracycline with TMA as the growth substrate.

To determine the optimal expression levels for the genome editing machinery, the transcription of Cas9 was varied by selecting transformants on media with increasing concentrations of tetracycline, and of the sgRNA by plating on media with either methanol (induced) or trimethylamine (TMA; repressed) as growth substrates. Surprisingly, no significant difference in genome editing efficiency was observed (FIG. 4A). In fact, the basal level of transcription provided by the two promoters in the absence of the inducers was sufficient for effective editing (FIG. 4A). A control vector identical to pDN211 but lacking the sgRNA (pDN207) was used to estimate the efficiency of genome editing. The efficiency of genome editing was measured as the ratio of mutant recovery (i.e. plating efficiency of pDN211) relative to the plating efficiency of the control vector and was estimated on media with either methanol or TMA as growth substrates. Significantly, genome editing in these experiments was particularly efficient, with edited strains being obtained at frequencies of ca. 20-25% relative to the control (i.e. one in four cells that receive the plasmid undergo gene conversion) (FIG. 4B).

To examine the maximum size of deletions that can be reliably generated by a single sgRNA, repair templates were tested with 1 kb homology arms placed at varying distance from the sgRNA-directed DSB (FIG. 4C). The transformation efficiency remained steady for templates that are 250 bp away from each end of the DSB, but declined precipitously when the distance increased beyond this point (FIG. 4C). Thus, a single sgRNA can be reliably used to delete up to 0.5 kbp of the chromosome, although larger deletions (up to 1 kbp) can be produced at the expense of efficiency.

Figure 5:
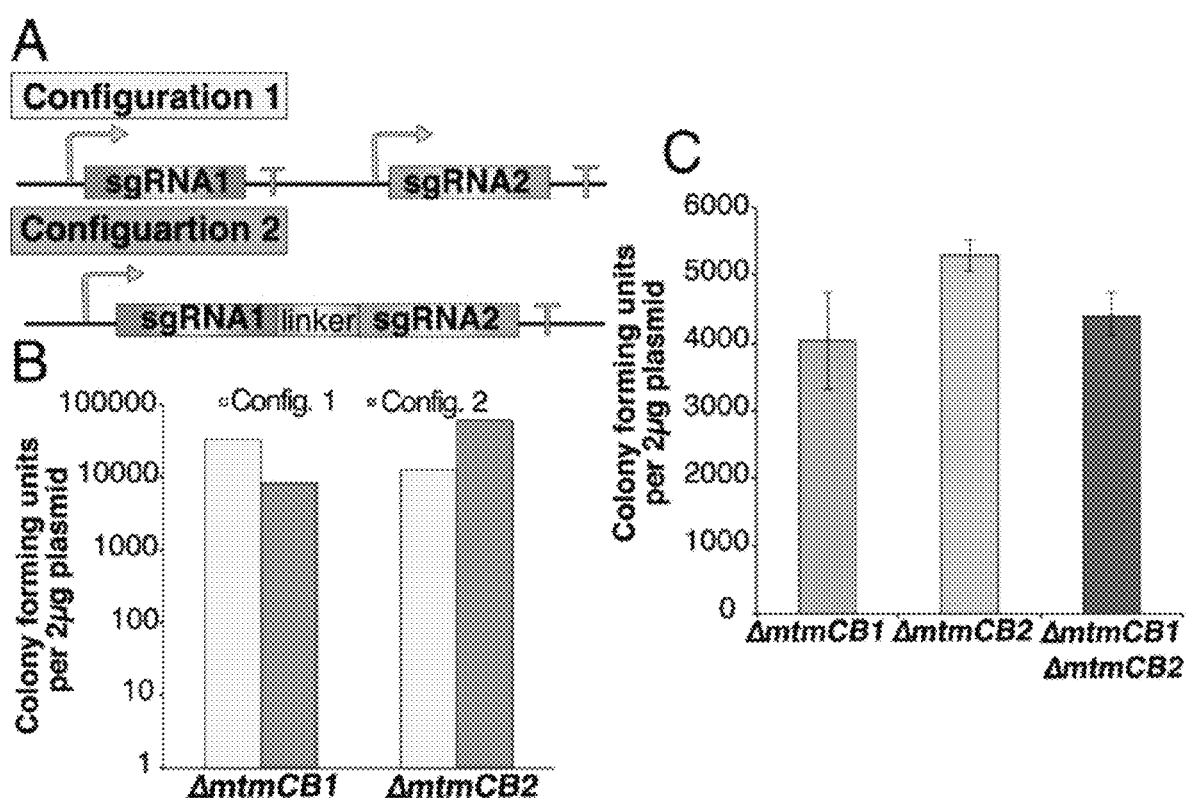
FIG. 5 shows simultaneous expression of multiple sgRNAs and generation of multiple mutations in *M. acetivorans*. (A) Two configurations for the expression of multiple sgRNAs were tested: in configuration one each sgRNA contains an individual promoter, whereas in configuration two a single promoter drives the expression of multiple sgRNAs separated by a 30-bp linker sequence. (B) Mean transformation efficiency of plasmids with sgRNAs in configuration one (light gray) or two (dark gray) configurations to delete either mtmCB1 or mtmCB2. Note: two independent transformation reactions were performed per plasmid. (C) Mean transformation efficiencies of plasmids to generate either ΔmtmCB1 (green), ΔmtmCB2 (blue), or ΔmtmCB1ΔmtmCB2 (purple) simultaneously. The error bars represent one SD of the mean transformation efficiency for three independent transformation reactions. All transformations were plated on medium lacking tetracycline with methanol as the growth substrate.
Figure 6:
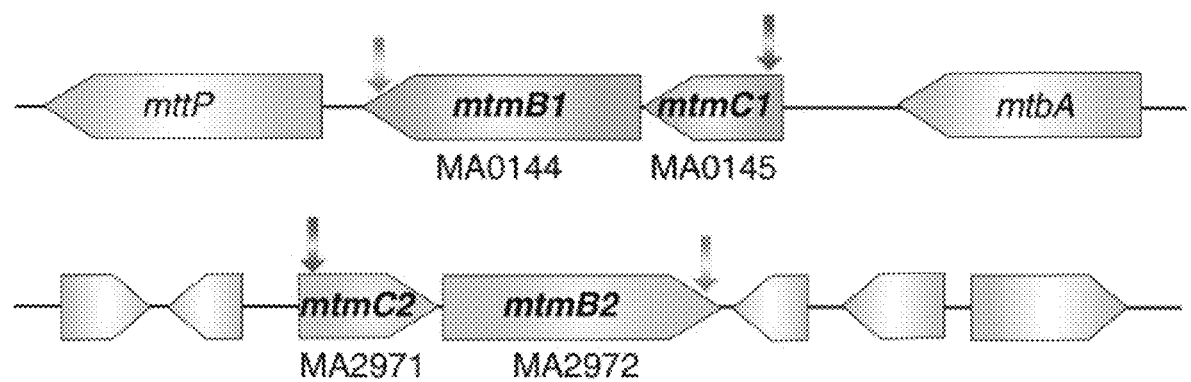
FIG. 6 shows genomic context of the isozymes encoding the monomethylamnie specific methyltransferases (mtmCB1 and mtmCB2) in *Methanosarcina acetivorans*. The genes encoding the corrinoid proteins MtmC1 and MtmC2 share 89% amino acid identity, whereas the genes encoding the methyltransferase MtmB1 and MtmB2 share 95% amino acid identity. The orange and pink arrows indicate the location of the two sgRNAs used to generate an in-frame deletion.
Figure 7:
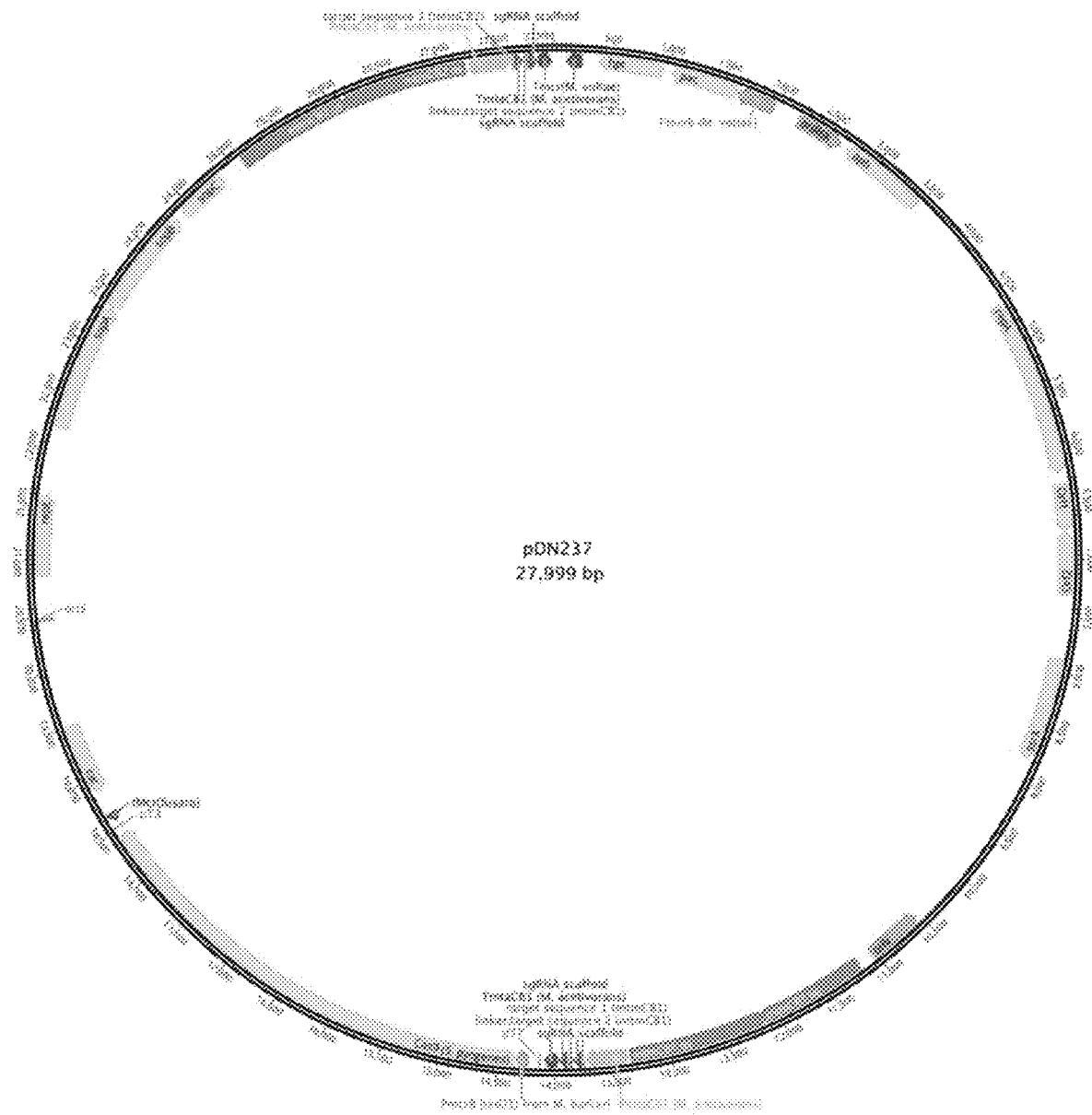
FIG. 7 shows Plasmid map of pDN237. The plasmid pDN237 contains the appropriate sgRNAs and homology repair templates to generate in-frame deletions in mtmCB1 and mtmCB2 simultaneously. The plasmid map was generated using Geneious version R9.

Example 3. Multiplex Expression of sgRNAs in *M. acetivorans* Enables Simultaneous Introduction of Multiple Mutations To explore the possibility of using multiple Cas9-mediated DSBs to create larger deletions, or to simultaneously introduce more than one mutation, two alternate arrangements for the expression of multiple sgRNAs were tested. In the first, sgRNAs were expressed individually, while in the second they were expressed as a single transcript separated by a 30 bp linker sequence (FIG. 5A). Plasmids with sgRNAs in either arrangement were equally efficient in generating strains with complete deletions (ca. 2 kbp) of the mtmCB1 and mtmCB2 loci, which are highly homologous genes encoding monomethylamine methyltransferase isozymes (FIG. 5B & FIG. 6). Thus, to reduce the size of mutagenic plasmids and simultaneously simplify their design, the placement of sgRNAs on a single transcript was preferred. Subsequently, a plasmid was generated containing all four sgRNAs and each of the corresponding repair templates to simultaneously delete mtmCB1 and mtmCB2 (FIG. 7). Surprisingly, transformants that simultaneously acquired both the ΔmtmCB1 and ΔmtmCB2 mutation were obtained at the same frequency as transformants that acquired only one of two mutations (FIG. 5C). Furthermore, the genomes of two random, independent isolates each for the ΔmtmCB1, ΔmtmCB2, and ΔmtmCB1ΔmtmCB2 mutants were completely sequenced and no off-target activity was detected (Table 1). This is especially notable given the high levels of homology between the sgRNA target sites in the two genes (FIGS. 8A & 8B). Hence, Cas9-mediated genome editing is remarkably precise in *M. acetivorans*.

tightly regulated gene expression and highly efficient chromosomal integration of cloned genes for *Methanosarcina* species. Archaea 2(3):193-203; Rother M, Boccazzi P, Bose A, Pritchett M A, Metcalf W W (2005) Methanol-dependent gene expression demonstrates that methyl-coenzyme M reductase is essential in *Methanosarcina acetivorans* C2A and allows isolation of mutants with defects in regulation of the methanol utilization pathway. J Bacteriol 187(16):5552-

TABLE 1

List of mutations in genome-edited strains containing in-frame deletions in mtmCB1 and/or mtmCB2.

| Position | Mutation | WWM984 | WWM985 | WWM986 | WWM987 | WWM988 | WWM989 | Notes |
|---|---|---|---|---|---|---|---|---|
| 171197 | Δ1,989 bp | Yes | Yes | No | No | Yes | Yes | ΔmtmCB1 |
| 487691 | C added | Yes | Yes | Yes | Yes | Yes | Yes | Present in WWM60 |
| 736484 | A→G (Y10Y) | No | No | No | No | Yes | No | Unique to WWM988 |
| 941168 | A5→6 | Yes | Yes | Yes | Yes | Yes | Yes | Present in WWM60 |
| 1314120 | Δ1 bp | Yes | Yes | Yes | Yes | Yes | Yes | Present in WWM60 |
| 1912669 | C→T (P7S) | No | Yes | No | No | No | No | Unique to WWM985 |
| 2086881-82 | TC→CT | Yes | Yes | Yes | Yes | Yes | Yes | Present in WWM60 |
| 2086886 | G→T | Yes | Yes | Yes | Yes | Yes | Yes | Present in WWM60 |
| 2412860 | G→T (P107H) | No | Yes | No | No | No | No | Unique to WWM985 |
| 2534543 | C added | Yes | Yes | Yes | Yes | Yes | Yes | Present in WWM60 |
| 2836646 | A→G (F64L) | Yes | Yes | Yes | Yes | Yes | Yes | Present in WWM60 |
| 2867059 | T→G (H313Q) | Yes | Yes | Yes | Yes | Yes | Yes | Present in WWM60 |
| 3433201 | Δ1 bp | Yes | Yes | Yes | Yes | Yes | Yes | Present in WWM60 |
| 3638887 | G→A (Y525Y) | Yes | No | No | Yes | No | Yes | Present in WWM60 |
| 3707136 | Δ1,633 bp | No | No | Yes | Yes | Yes | Yes | ΔmtmCB2 |
| 4295452 | Δ1 bp | Yes | Yes | Yes | Yes | Yes | Yes | Present in WWM60 |
| 4874567 | Δ1 bp | Yes | Yes | Yes | Yes | Yes | Yes | Present in WWM60 |
| 4945345 | C added | Yes | Yes | Yes | Yes | Yes | Yes | Present in WWM60 |
| 5078585 | G→A (M1M) | Yes | Yes | Yes | Yes | Yes | Yes | Present in WWM60 |

Example 4. Insertion of Large DNA Segments Via Cas9-Dependent Genome Editing

Figure 9:
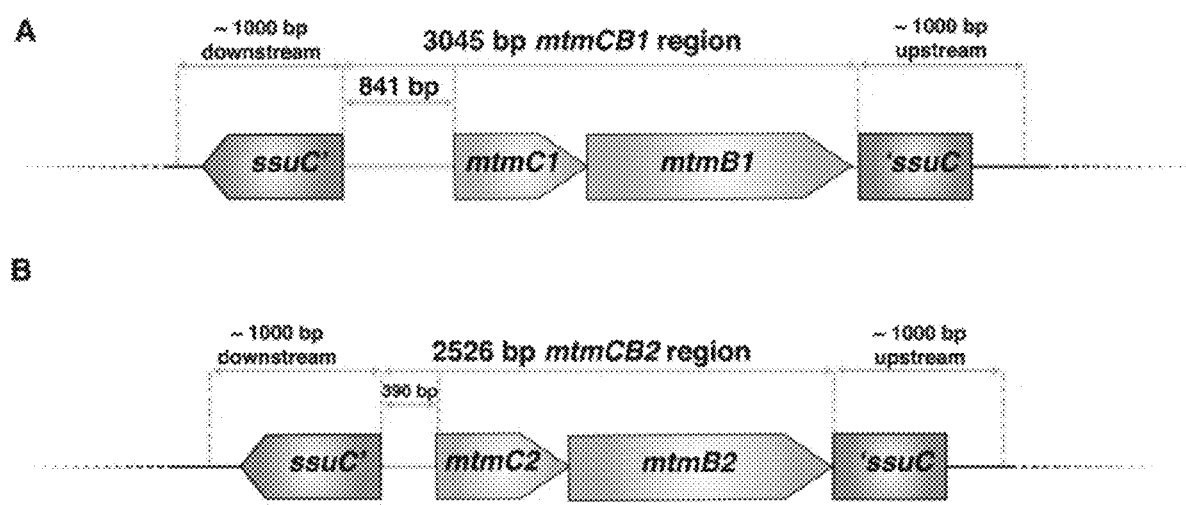
FIG. 9 shows design of repair templates for Cas9-mediated gene insertions at the ssuC locus in *M. acetivorans*. (A) Homology repair template to insert the mtmCB1 operon (green) and an 840-bp region upstream (likely to contain the putative promoter) within the ssuC CDS. (B) Homology repair template to insert the mtmCB2operon (blue) and a 390-bp region upstream (likely to contain the putative promoter) within the ssuC CDS.

To assess the efficacy of gene knock-ins, plasmids designed to insert either a 3.05 kbp fragment containing the mtmCB1 locus or a 2.53 kbp fragment containing the mtmCB2 locus were constructed and used to introduce wild-type copies of each gene into the ssuC gene of the ΔmtmCB1ΔmtmCB2 double mutant (FIGS. 9A & 9B). Although 20-60% fewer transformants were observed (relative to the simple 34 bp deletion mutation described above) all transformants screened contain the desired gene insertions.

Example 5. A Cas9-Dependent Genetic Screen to Test for Gene Essentiality

Two methods have previously been employed to test gene essentiality in *Methanosarcina* (Guss A M, Rother M, Zhang J K, Kulkarni G, Metcalf W W (2008) New methods for 5559); however, both approaches are laborious and time-consuming. Therefore, the use the efficient repair of the DSB generated by the Cas9-sgRNA complex was tested to assay gene essentiality in *M. acetivorans*. For non-essential genes (ssuC, mtmCB1, mtmCB2), $10^3$-$10^4$ fold more transformants are consistently observed when a repair template to generate a deletion is provided in addition to the sgRNA-Cas9 complex. It was expected that this would not be true for essential genes, because HDR-directed repair using a deletion cassette would also be lethal. To test this idea, plasmids were constructed with and without a repair template that target the previously established essential genes mcrA and hdrED (Guss A M, Rother M, Zhang J K, Kulkarni G, Metcalf W W (2008) New methods for tightly regulated gene expression and highly efficient chromosomal integration of cloned genes for *Methanosarcina* species. Archaea 2(3):193-203; Buan N R, Metcalf W W (2010) Methanogenesis by *Methanosarcina acetivorans* involves two structurally and functionally distinct classes of heterodisulfide reductase. *Mol Microbiol* 75(4):843-853).

In contrast to the results with the non-essential ssuC, mtmCB1 and mtmCB2 loci, where thousands of transformants were obtained in the presence of a repair template, plasmids that targeted the essential genes generated less than five transformants, regardless of whether a repair template is present (Table 2). Thus, the ratio of transformants obtained in the presence versus absence of a repair template can be used as a reliable and simple test for gene essentiality in *M. acetivorans*.

TABLE 2

Using Cas9-mediated genome editing as a screen for gene essentiality in *M. acetivorans*.

| Gene/operon | Transformation efficiency of plasmids with genome editing machinery | |
| --- | --- | --- |
| | Repair template absent | Repair template present |
| ssuC | 4 ± 3 | 19,040 ± 4,255 |
| mtmCB1 | <1 | 4,033 ± 716 |
| mtmCB2 | Not tested | 5,300 ± 235 |
| mcrA | 2 ± 1 | <1 |
| hdrED | <1 | 0 |

Transformation efficiencies indicate the mean ± 1 SD of puromycin resistant colonies for three independent transformations.

Example 6. Heterologous Expression of NHEJ Genes Leads to Template-Independent Repair in *M. acetivorans*

Figure 10:
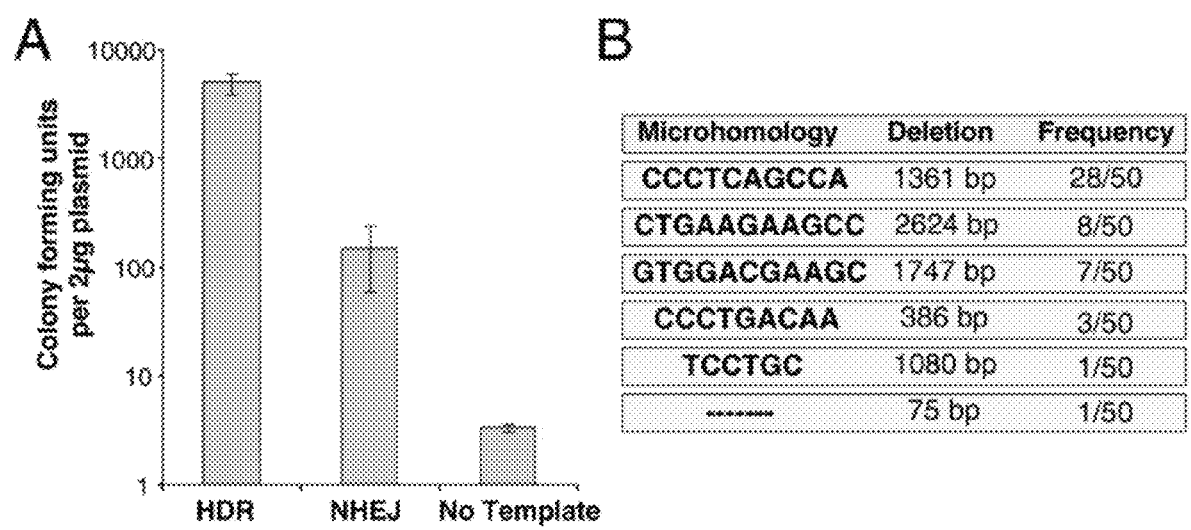
FIG. 10 shows coexpression of NHEJ genes with the Cas9-sgRNA complex in *M. acetivorans*. (A) Transformation efficiency of plasmids with a sgRNA targeting the ssuC locus containing either a repair template for HDR-mediated DSB repair, the NHEJ genes, or no repair template. The error bars represent one SD of the mean transformation efficiency for three independent transformation reactions. All transformations were plated on medium lacking tetracycline with TMA as the growth substrate. (B) Regions of naturally occurring microhomology surrounding the ssuC locus at which NHEJ-mediated deletions were observed in Pur$^R$ transformants. CCCTCAGCCA is SEQ ID NO:48; CTGAAGAAGCC is SEQ ID NO:49; GTGGACGAAGC is SEQ ID NO:50; CCCTGACAA is SEQ ID NO:51; and TCCTGC is SEQ ID NO:52.
Figure 11:
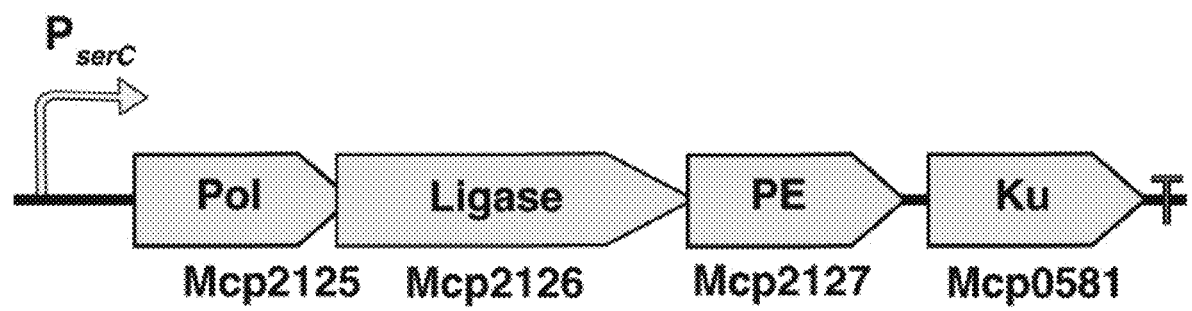
FIG. 11 shows heterologous expression of the NHEJ genes from *Methanocella paludicola*. Design of a 3.25-kbp artificial operon with the NHEJ polymerase (Mcp_2125), DNA ligase (Mcp_2126), phosphoesterase (Mcp_2127), and Ku (Mcp_0581) genes from *M. paludicola* SANAE fused to the *Methanosarcina barkeri* Fusaro serC promoter and followed by the *M. acetivorans* Mcr terminator.

A lethal phenotype for plasmids expressing a Cas9-sgRNA complex in the absence of a repair template was uniformly observed across a wide range of sgRNAs tested, suggesting that NHEJ does not occur in *M. acetivorans* (Table 2). This result is consistent with the absence of genes related to Ku and LigD in the completely sequenced genome. Galagan J E, et al. (2002) The Genome of *M. acetivorans* reveals extensive metabolic and physiological diversity. *Genome Res.* 12(4):532-542. Nevertheless, in some circumstances HDR-independent gene editing would be very useful. Therefore, it was examined whether NHEJ could be established in *Methanosarcina* for use in conjunction with the Cas9-sgRNA complex. For this purpose, the NHEJ machinery from the closely related methanogen *Methanocella paludicola* was used. An artificial operon encoding four *M. paludicola* NHEJ proteins (DNA ligase (Lig), polymerase (Pol), phosphoesterase (PE), and Ku) was synthesized and transcriptionally fused to the moderately expressed serC promoter to allow transcription in *M. acetivorans* (FIG. 11). This cassette was then added to the Cas9 ssuC-targeting vector without a repair template. Transformation with this plasmid was ca. 100-fold less efficient than the corresponding HDR vector, but ca. 10-fold higher than with plasmids lacking the NHEJ system (FIG. 10A). Therefore, expression of the *M. paludicola* NHEJ machinery overcame the lethal effect of the Cas9 ssuC-targeting vector without a repair template. Molecular analysis of the ssuC locus in these transformants revealed deletions ranging from 75 bp to 2.7 kb in length, often occurring at naturally occurring regions of microhomology 6-11 bp in length (FIG. 10B). Thus, the combined Cas9/NHEJ system provides the opportunity to generate a variety of mutations surrounding a single target site. Importantly, these plasmids are much simpler to construct, requiring only addition of target-specific sgRNA. It was examined if the addition of two sgRNAs targeting DNA sequences ca. 450 bp apart in conjunction with NHEJ could be used to generate precise deletions without a repair template. Interestingly, attempts to construct ssuC deletions via this method were not successful: only a handful of colonies were obtained (6±3 per 2 μg plasmid) and none had the precise deletion desired. We examined 20 transformants obtained by this method. Two contained a 1.3 kb deletion of the ssuC locus, which occurred at a region of microhomology (FIG. 10B). The remainder had wild-type copies of the ssuC gene and, thus, are likely to be so-called escape mutants in which the Cas9 gene or sgRNA has mutated on the targeting plasmid.

These Cas9-based tools have a transformative impact on the speed, scope and scale of research that can be accomplished in the Archaea and methanogens, such as *M. acetivorans*. Most notably, multiplexed gene editing plasmids enables generation of strains with multiple mutations, ranging from SNPs to large indels, in a matter of weeks versus years. These tools enable researchers to swiftly tag genes at their native loci on the host chromosome, allowing the study of context-specific gene expression, "pull-down" experiments to establish protein-protein and protein-DNA interaction networks, and purification of proteins that contain unique amino acids or novel post-translational modifications. Srinivasan G, James C M, Krzycki J A. (2002) Pyrrolysine encoded by UAG in Archaea: charging of a UAG-decoding specialized tRNA. *Science* 296(5572):1459-1462; Kahnt J, et al. (2007) Post-translational modifications in the active site region of methyl-coenzyme M reductase from methanogenic and methanotrophic archaea. *FEBS J* 274(18):4913-4921.

Furthermore, deleting a gene of interest using a NHEJ-based technique is very cost-effective, as it simply requires the insertion of a commercially synthesized DNA fragment containing the appropriate sgRNA(s) into pDN243, the vector containing Cas9 and the NHEJ machinery. Thus, studies that were previously inconceivable, such as constructing a library of strains with single-gene deletions in every non-essential gene on the *M. acetivorans* chromosome are now feasible, in terms of both time and cost. Finally, minor modifications enable the application of this approach to a broad range of methanogens and other archaea.

Certain features of Cas9-mediated genome editing in *M. acetivorans* are particularly unique and noteworthy. For instance, unlike eukaryotes, targeting of the Cas9-sgRNA complex to a particular chromosomal region in *M. acetivorans* is remarkably precise as no off-target activity was observed upon resequencing multiple, independent genome-edited mutants (Table 1). Since the *M. acetivorans* genome (ca. 5.75 Mbp) is 10-100 fold smaller in comparison to eukaryotic genomes, it is possible that fewer off-target sites are present. However, no off-target activity could be detected despite the intentional choice of highly similar sgRNA targets in the mtmCB isozymes (FIGS. 8A & 8B). Thus, it is likely that properties of the Cas9-sgRNA complex, including target specificity, vary significantly across domains of life, perhaps due to differences in chromosomal organization and DNA repair machinery. Notably, unlike the Cas9-mediated genome editing in bacteria, a high rate of HDR was observed for the Cas9-mediated DSB and a very low frequency of 'escape' mutants. These key distinctions are likely to stem from evolutionarily distinct HDR machinery. Archaeal DNA repair involves homologs of the eukaryotic proteins Mre11 and Rad50, and two other unique proteins HerA and NurA, which perform end-resection after a DSB occurs. Subsequently, the RecA orthologs RadA and RadB, again more closely related to recombination proteins of eukaryotes, mediate strand invasion. Finally, Hjc, unrelated to the RuvABC complex in bacteria, is involved in the resolution of the Holliday junction. Therefore, co-expression of archaeal HDR machinery along with an RNA-guided DNA endonuclease can be used to overcome some of the obstacles that have been reported in recent bacterial work.

Similar host-specific effects upon heterologous expression of the NHEJ machinery from *Methanocella paludicola* in *M. acetivorans* was observed. These archaeal proteins have biochemical activities that are strikingly similar to the well-characterized bacterial Ku and LigD of *Mycobacterium tuberculosis*. The robust template-independent repair they conferred when co-expressed with the Cas9-sgRNA complex in *M. acetivorans* was surprising (FIG. 10A). These data are in sharp contrast to a recent study in which co-expression of Ku and LigD from *M. tuberculosis* did not rescue the Cas9-mediated DNA break in *E. coli*. Cui L, Bikard D (2016) Consequences of Cas9 cleavage in the chromosome of *Escherichia coli*. *Nucleic Acids Res* 44(9): 4243-4251. Furthermore, tem plate-independent DNA repair happens at naturally occurring regions of microhomology (ranging from 6-11 bp), which supports a recent hypothesis that the archaeal NHEJ pathway conduct microhomology mediated end joining (MMEJ) in vivo. Bartlett E J, Brissett N C, Plocinski P, Carlberg T, Doherty J (2015) Molecular basis for DNA strand displacement by NHEJ repair polymerases. *Nucleic Acids Res* 44(5):2173-2186.

Thus, in addition to its application as a means of generating random site-specific mutations in *M. acetivorans*, this tool can also be used to dissect the archaeal MMEJ machinery in vivo. In this context, no particular sequence pattern or any distinct signature (GC content, nt frequency) could be inferred from the regions of microhomology at which repair occurred (FIG. 10B). Moreover, DNA repair mediated by MMEJ is almost completely abolished when two sgRNAs were simultaneously expressed, suggesting that the repair mechanism has the ability to distinguish breaks that occur at discrete loci.

Finally, we chose to use the well-established *S. pyogenes* Cas9-sgRNA complex for genome editing purposes over the native Type I or Type III CRISPR/Cas systems that are commonly found in *Methanosarcina* spp., as was done in *Sulfolobus islandicus* for two reasons. First, the CRISPR/Cas subtypes vary significantly across the genus *Methanosarcina*, even within strains belonging to the same species. Hence a genome editing technique reliant on the native CRISPR/Cas machinery for one strain might not work in other closely related strains. Recent studies across a wide-range of bacteria have revealed that anti-CRISPR proteins to silence the native CRISPR/Cas system are also often encoded on the chromosome. Although no anti-CRISPR proteins have been detected in *Methanosarcina*, it is possible that they exist and might potentially complicate use of the native CRISPR/Cas machinery for genome editing. Secondly, tweaking the native CRISPR/Cas machinery for genome editing purposes is likely to impact organismal physiology in an unpredictable fashion and skew genetic analyses downstream. Thus, we chose to deploy the simple, modular Cas9-mediated genome editing machinery on a vector that will be transiently maintained in methanogens such as *M. acetivorans*.

Example 7. Materials and Methods

Strains, Media, and Growth Conditions

All chemicals were purchased from Sigma-Aldrich (St. Louis, Mo.) unless specified. *Methanosarcina acetivorans* strains were grown in single-cell morphology (Sowers K R, Boone J E, Gunsalus R P (1993) Disaggregation of *Methanosarcina* spp. and growth as single cells at elevated osmolarity. *Appl Environ Microbiol* 59(11):3832-3839) at 37° C. in bicarbonate-buffered high salt (HS) liquid medium containing 125 mM methanol or 50 mM trimethylamine hydrochloride (TMA) in Balch tubes with $N_2/CO_2$ (80/20). Plating solid medium was conducted in an anaerobic glove chamber (Coy Laboratory Products, Grass Lake, Mich.) as described previously. Metcalf W W, Zhang J K, Shi X, Wolfe R S (1996) Molecular, genetic, and biochemical characterization of the serC gene of *Methanosarcina barkeri* Fusaro. *J Bacteriol* 178(19):5797-5802.

Solid media plates were incubated in an intra-chamber anaerobic incubator maintained at 37° C. with $N_2/CO_2/H_2S$ (79.9/20/0.1) in the headspace as described previously in (39). Puromycin (CalBiochem, San Diego, Calif.), the purine analog 8-aza-2,6-diaminopurine (8ADP) (R. I. Chemicals, Orange, Calif.) and bromoethane sulfonic acid (BES) were added to a final concentration of 2 µg/ml, 20 µg/ml, 0.4 mM respectively from sterile, anaerobic stock solutions. Anaerobic, sterile stocks of tetracycline hydrochloride in deionized water were prepared fresh shortly before use and added to a final concentration as indicated. *E. coli* strains were grown in LB broth at 37° C. with standard antibiotic concentrations. WM4489, a DH10B derivative engineered to control copy-number of oriV-based plasmids (Kim S Y, et al. (2012) Different biosynthetic pathways to fosfomycin in *Pseudomonas syringae* and *Streptomyces* species. Antimicrob Agents Chemother 56(8):4175-4183), was used as the host strain for all plasmids generated in this study (Table 3). Plasmid copy number was increased by adding sterile rhamnose to a final concentration of 10 mM.

TABLE 3

List of plasmids used in this study.

| Plasmid | Features | Source |
|---|---|---|
| pAMG40 | Vector for fosmid retrofitting that contains pC2A and λattB | (1) |
| pJK027A | Vector with PmcrB(tet01) promoter fusion to uidA that contains φC31-attB and λattP | (1) |
| pMJ806 | pET-based vector that contains the native Spy cas9 ORF | (2) |
| pDN201 | pJK027A-derived plasmid with PmcrB(tet01) promoter fusion to Spy cas9 | Present study |
| pDN202 | pDN201-derived plasmid with ssuC repair template containing 0.5-kb homology flanks | Present study |
| pDN203 | pDN201-derived plasmid with a synthetic fragment containing PmtaCB1 promoter fusion to a sgRNA targeting ssuC | Present study |
| pDN204 | pDN203-derived plasmid with ssuC repair template containing 0.5-kb homology flanks | Present study |
| pDN206 | Cointegrate of pDN201 and pAMG40 | Present study |

TABLE 3-continued

List of plasmids used in this study.

| Plasmid | Features | Source |
|---|---|---|
| pDN207 | Cointegrate of pDN202 and pAMG40 | Present study |
| pDN208 | Cointegrate of pDN203 and pAMG40 | Present study |
| pDN209 | Cointegrate of pDN204 and pAMG40 | Present study |
| pDN210 | pDN203-derived plasmid with ssuC repair template containing 1-kb homology flanks | Present study |
| pDN211 | Cointegrate of pDN210 and pAMG40 | Present study |
| pDN215 | pDN203-derived plasmid with ssuC repair template containing 1-kb homology flanks that are 100 bp from each end of the sgRNA-directed DSB | Present study |
| pDN216 | pDN203-derived plasmid with ssuC repair template containing 1-kb homology flanks that are each 250 bp from each end of the sgRNA-directed DSB | Present study |
| pDN217 | pDN203-derived plasmid with ssuC repair template containing 1-kb homology flanks that are each 500 bp from each end of the sgRNA-directed DSB | Present study |
| pDN218 | Cointegrate of pDN215 and pAMG40 | Present study |
| pDN219 | Cointegrate of pDN216 and pAMG40 | Present study |
| pDN220 | Cointegrate of pDN217 and pAMG40 | Present study |
| pDN221 | pDN201-derived plasmid with two synthetic fragments: one containing PmtaCB1 promoter fusion to sgRNA targeting mtmB1 and another containing PmtaCB1 promoter fusion to sgRNA targeting mtmC1 | Present study |
| pDN222 | pDN201-derived plasmid with two synthetic fragments: one containing PmtaCB1 promoter fusion to sgRNA targeting mtmB1 and another with a 30-bp linker sequence and a sgRNA targeting mtmC1 | Present study |
| pDN223 | Cointegrate of pDN221 and pAMG40 | Present study |
| pDN224 | Cointegrate of pDN222 and pAMG40 | Present study |
| pDN225 | pDN221-derived plasmid with a repair template with 1-kb homology flanks to delete mtmCB1 | Present study |
| pDN226 | pDN222-derived plasmid with a repair template containing 1-kb homology flanks to delete mtmCB1 | Present study |
| pDN227 | Cointegrate of pDN225 and pAMG40 | Present study |
| pDN228 | Cointegrate of pDN226 and pAMG40 | Present study |
| pDN229 | pDN201-derived plasmid with a repair template containing 1-kb homology flanks to delete mtmCB2 | Present study |
| pDN230 | pDN229-derived plasmid with two synthetic fragments: one containing PmtaCB1 promoter fusion to sgRNA targeting mtmC2 and another containing PmtaCB1 promoter fusion to sgRNA targeting mtmB2 | Present study |
| pDN231 | pDN229-derived plasmid with two synthetic fragments: one containing PmtaCB1 promoter fusion to sgRNA targeting mtmC2 and another containing a linker sequence and a sgRNA targeting mtmB2 | Present study |
| pDN232 | Cointegrate of pDN230 and pAMG40 | Present study |
| pDN233 | Cointegrate of pDN231 and pAMG40 | Present study |
| pDN234 | pDN225-derived plasmid with a region from pDN230 containing the mtmCB2 repair template and sgRNAs | Present study |
| pDN235 | pDN226-derived plasmid with a region from pDN231 containing the mtmCB2 repair template and sgRNAs | Present study |
| pDN236 | Cointegrate of pDN234 and pAMG40 | Present study |
| pDN237 | Cointegrate of pDN235 and pAMG40 | Present study |
| pDN238 | pDN203-derived plasmid with a repair template to insert a 3.05-kbp fragment encoding mtmCB1 within the ssuC CDS | Present study |
| pDN239 | Cointegrate of pDN238 and pAMG40 | Present study |
| pDN240 | pDN203-derived plasmid with a repair template to insert a 2.53-kbp fragment encoding mtmCB2 within the ssuC CDS | Present study |
| pDN241 | Cointegrate of pDN240 and pAMG40 | Present study |
| pDN242 | pDN203-derived plasmid containing a PserC promoter fusion to all four NHEJ genes from *M. paludicola* | Present study |
| pDN243 | Cointegrate of pDN242 and pAMG40 | Present study |
| pDN254 | pDN201-derived plasmid with two synthetic fragments: one containing PmtaCB1 promoter fusion to sgRNA targeting ssuC and another containing a linker sequence and a second sgRNA targeting ssuC 450 bp away from the cut-site of the first sgRNA | Present study |

TABLE 3-continued

List of plasmids used in this study.

| Plasmid | Features | Source |
|---|---|---|
| pDN255 | pDN254-derived plasmid containing a PserC promoter fusion to all four NHEJ genes from M. paludicola | Present study |
| pDN256 | Cointegrate of pDN254 and pAMG40 | Present study |
| pDN257 | Cointegrate of pDN255 and pAMG40 | Present study |
| pDN258 | pDN201-derived plasmid with two synthetic fragments: one containing PmtaCB1 promoter fusion to one sgRNA targeting mcrA and another containing a linker sequence and a second sgRNA targeting mcrA 1.4 kbp away from the first sgRNA | Present study |
| pDN259 | pDN258-derived plasmid with a repair template containing 1-kb homology flanks to delete mcrA | Present study |
| pDN260 | Cointegrate of pDN258 and pAMG40 | Present study |
| pDN261 | Cointegrate of pDN259 and pAMG40 | Present study |
| pDN268 | pDN201-derived plasmid with two synthetic fragments: one containing PmtaCB1 promoter fusion to sgRNA targeting hdrE and another containing a linker sequence and a sgRNA targeting hdrD | Present study |
| pDN269 | pDN258-derived plasmid with a repair template containing 1 kb homology flanks to delete hdrED | Present study |
| pDN270 | Cointegrate of pDN268 and pAMG40 | Present study |
| pDN271 | Cointegrate of pDN269 and pAMG40 | Present study |

1. Guss AM, Rother M, Zhang JK, Kulkarni G, Metcalf WW (2008) New methods for tightly regulated gene expression and highly efficient chromosomal integration of cloned genes for *Methanosarcina* species. *Archaea* 2(3):193-203.
2. Jinek M, et al. (2012) A Programmable Dual-RNA-Guided DNA endonuclease in adaptive bacterial immunity. *Science* 337(6096):816-822.

Plasmids

All plasmids used in this study are listed in Table 3. The plasmid pMJ0806 was obtained from Jennifer Doudna (Addgene plasmid #39312). The *Streptococcus pyogenes* (Spy) Cas9 ORF was fused to the PmcrB(tetO1) promoter in pJK027A linearized with NdeI and HindIII by the Gibson assembly method as described previously. Gibson D G, et al. (2009) Enzymatic assembly of DNA molecules up to several hundred kilobases. *Nat Methods* 6(5):343-345.

The DNA segments containing sgRNA(s) flanked by putative mtaCB1 promoter and terminator sequences from *M. acetivorans* were synthesized as double-stranded DNA fragments ('gBlocks') from Integrated DNA Technologies (Coralville, Iowa) and used for cloning purposes per manufacturer's instructions. A 3.25 kbp artificial operon with the NHEJ polymerase (Mcp_2125), DNA ligase (Mcp_2126), phosphoesterase (Mcp_2127), and Ku (Mcp_0581) genes from *Methanocella paludicola* SANAE fused to the *Methanosarcina barkeri* Fusaro serC promoter was ordered from the GeneArt gene synthesis service (Life Technologies (Carlsbad, Calif.). All synthetic DNA fragments and repair templates were introduced in the appropriate vector backbone linearized with either AscI or PmeI by the Gibson assembly method as described previously. Gibson D G, et al. (2009) Enzymatic assembly of DNA molecules up to several hundred kilobases. *Nat Methods* 6(5):343-345.

The entire pC2A plasmid was introduced in the appropriate pJK027A-derived vector (carrying the λattB site) by retrofitting with pAMG40 (carrying the λattP site) using the BP Clonase II master mix (Invitrogen, Carlsbad, Calif.) per the manufacturer's instructions. WM4489 was transformed by electroporation at 1.8 kV using an E. coli Gene Pulser (Bio-Rad, Hercules, Calif.). Standard techniques were used for the isolation and manipulation of plasmid DNA. All pJK027A-derived plasmids were verified by Sanger sequencing at the Roy J. Carver Biotechnology Center, University of Illinois at Urbana-Champaign and all pAMG40 cointegrates were verified by restriction endonuclease analysis. Primers used in this study are listed in Table 4. The plasmid sequence and annotations for pDN211 have been submitted to Genbank (Accession number KY436376).

TABLE 4

List of primers used in this study.

| Primer | Sequence (underlined region indicates overhangs for Gibson assembly) |
|---|---|
| Cas9f_f | TTTTAATAAATTAAGGAGGAAATTCATATGGATAAGAAATACTCAATAGGCT (SEQ ID NO: 1) |
| Cas9_r | CATACATTATACGAAGTTATCAAGAAGCTTTCAGTCACCTCCTAGCTGACT (SEQ ID NO: 2) |
| ssuC_ds_f (500 bp) | TCCTTTTGGAGCCTTTTTTTTTCGAAGTTTAAACATC CAT CCT GTG CAG GTA GT (SEQ ID NO: 3) |
| ssuC_ds_r (500 bp) | GCGGCCGC GAA TAA ATT GCT TCT TCC GAG T (SEQ ID NO: 4) |

TABLE 4-continued

List of primers used in this study.

| Primer | Sequence (underlined region indicates overhangs for Gibson assembly) |
|---|---|
| ssuC_us_f (500 bp) | TCTCCTCCGATTGTTTTTAAAGGCGGCCGC GGC GAT TGC GAA TAT AAG AGA (SEQ ID NO: 5) |
| ssuC_us_r (500 bp) | GGCCGCGATCGCCGGCGCGCCTGCAGGTTTAAACGC AAT GGA CGT TCG ATT GTA (SEQ ID NO: 6) |
| ssuC_ds_f (1,000 bp) | TCCTTTTGGAGCCTTTTTTTTTCGAAGTTTAAACGGC GAT TGC GAA TAT AAG AG (SEQ ID NO: 7) |
| ssuC_ds_r (1,000 bp) | GCGGCCGC AGC TGA ACT TCG GCT ATC AG (SEQ ID NO: 8) |
| ssuC_us_f (1,000 bp) | GGGTACTCGGCTGATAGCCGAAGTTCAGCTGCGGCCGCTAC GAA GAT AGA TAC GGC CAG (SEQ ID NO: 9) |
| ssuC_us_r (1,000 bp) | GGCCGCGATCGCCGGCGCGCCTGCAGGTTTAAACCGA TGG CAT CTA TAA GGC TG (SEQ ID NO: 10) |
| mtmCB1_ds_f | GGACGCATCGTGGCCGGATCTTGCGGCCGCAGT ACC GAA CAT AGA TAG AG (SEQ ID NO: 11) |
| mtmCB1_ds_r | CTT GTA TTC TAA GCC GAA AG (SEQ ID NO: 12) |
| mtmCB1_us_f | TCAGGTCGAACTTTCGGCTTAGAATACAAGATT TTG AGT TGC GAT CGC GTT G (SEQ ID NO: 13) |
| mtmCB1_us_r | CGATACCGTCAAAACTTCATTTTTAATTTTTGCGGCCGCAGC GCC AAT CTC CAG AAA ATG (SEQ ID NO: 14) |
| mtmCB2_us_f | CCTTTTGGAGCCTTTTTTTTTCGAAGTTTAAACCAT CTG TCC TCA TGC AAG GTG (SEQ ID NO: 15) |
| mtmCB2_us_r | CCTATTGACATTATCACAAAGGGCCTCTCCGTT GCC TCA GCA AAG GGT GTT G (SEQ ID NO: 16) |
| mtmCB2_ds_f | GTT GCC TCA GCA AAG GGT GTT G (SEQ ID NO: 17) |
| mtmCB2_ds_r | GCCGCGATCGCCGGCGCGCCTGCAGGTTTAAACCTC CCT ACC AAT CTC CGA TAA CC (SEQ ID NO: 18) |
| mtmCB1_repair_sgRNAs_f | TGGTTACCCAGGCCGTGCCGGCACGTTAACCAT CTG TCC TCA TGC AAG GTG C (SEQ ID NO: 19) |
| mtmCB1_repair_sgRNAs_r | CACACTTGCATCGGATGCAGCCCGGTTAACTAC ATG AGG GCT GAA AAG CCG (SEQ ID NO: 20) |
| mcrA_ds_f | CCTTTTGGAGCCTTTTTTTTTCGAAGTTTAAACATT CTC TCC TCT GGC AGA ACA G (SEQ ID NO: 21) |
| mcrA_ds_r | GT CAT CCC GGC AAA ATA AAC (SEQ ID NO: 22) |
| mcrA_us_f | GATTTATTGAGTTTATTTTGCCGGGATGACCAT CGG GTT GTA GAA TGC AAT G (SEQ ID NO: 23) |
| mcrA_ds_r | GATGTTGTTGGCGCGCCTGCAGGTTTAAACGTC CCA GGG ATA AAC TAA ATT C (SEQ ID NO: 24) |
| hdrED_us_f | CCTTTTGGAGCCTTTTTTTTTCGAAGTTTAAACATG GCT GTT TCA GGT TGT CC (SEQ ID NO: 25) |
| hdrED_us_r | GAA GTA TGC CAT CTC ACT GC (SEQ ID NO: 26) |
| hdrED_ds_f | TAAATTATTAGCAGTGAGATGGCATACTTCTCG GGC TCA GCG TAG AGT AAC (SEQ ID NO: 27) |
| hdrED_ds_r | GATGTTGTTGGCGCGCCTGCAGGTTTAAACCGC ATA CAA TGA GGG GCA AGG (SEQ ID NO: 28) |

In Silico Design of Target Sequences

All target sequences used in this study are listed in Table 5. Target sequences were designed using the CRISPR site finder tool in Geneious version R9. Kearse M, et al. (2012) Geneious Basic: An integrated and extendable desktop software platform for the organization and analysis of sequence data. *Bioinformatics* 28(12):1647-1649. The *M. acetivorans* chromosome and the plasmid pC2A were used to score off-target binding sites.

TABLE 5

List of target sequences used in this study.

| Gene (locus tag) | Target sequence (+ PAM) | Position on *M. acetivorans* chromosome |
|---|---|---|
| ssuC (MA0064) | ATC CGC TGC AAA CTG CCA TA TGG (SEQ ID NO: 29) | 73479-73498 (+ strand) |
| ssuC (MA0064) | CTG AGG GAA TCG CAA CAA AA CGG (SEQ ID NO: 30) | 73037-73056 (+ strand) |
| mtmC1 (MA0145) | AGGT TGC GCA CAG TTA GCC C AGG (SEQ ID NO: 31) | 173167-173186 (- strand) |
| mtmB1 (MA0144) | AAG GAA GAA GCT CGA AGA CC TGG (SEQ ID NO: 32) | 171211-1721230 (- strand) |
| mtmC2 (MA2971) | CTG AGG CAG AAA GAT CTC TG CGG (SEQ ID NO: 33) | 3707170-3707189 (- strand) |
| mtmB2 (MA2972) | GAG GAG GCA CAT CTC CGT AC CGG (SEQ ID NO: 34) | 3708692-3708711 (- strand) |
| mcrA (MA4546) | TGA ACT CTC TGA TGG CAC CG CGG (SEQ ID NO: 35) | 5596716-5596735 (+ strand) |
| mcrA (MA4546) | GAT TGC ACG CTG ACC GAG AG GGG (SEQ ID NO: 36) | 5598139-5598158 (+ strand) |
| hdrD (MA0688) | GAG AGT CAC GAC CAT CCA TA AGG (SEQ ID NO: 37) | 805287-805306 (- strand) |
| hdrE (MA0687) | TTA TCT GGA CAA ACG TCA GT CGG (SEQ ID NO: 38) | 803399-803418 (- strand) |

Transformation of *M. acetivorans*

All *M. acetivorans* strains used in this study are listed in Table 6. Liposome-mediated transformation was used for *M. acetivorans* as described previously in (Metcalf et al. (1997) A genetic system for Archaea of the genus *Methanosarcina*: Liposome-mediated transformation and construction of shuttle vectors. 94(6):2626-2631) and 10 ml of late-exponential phase culture of *M. acetivorans* and 2 μg of plasmid DNA were used for each transformation.

TABLE 6

List of *Methanosarcina acetivorans* strains used in this study

| Strain | Genotype | Construction details | Source |
|---|---|---|---|
| WWM60 | Δhpt::PmcrB-tetR | — | (1) |
| WWM984 | Δhpt::PmcrB-tetR, ΔmtmCB1 | WWM60 was transformed to Pur$^R$ with pDN227; plasmid-cured strain was isolated by plating on medium with 8ADP | Present study |
| WWM985 | Δhpt::PmcrB-tetR, ΔmtmCB1 | WWM60 was transformed to Pur$^R$ with pDN228; plasmid-cured strain was isolated by plating on medium with 8ADP | Present study |
| WWM986 | Δhpt::PmcrB-tetR, ΔmtmCB2 | WWM60 was transformed to Pur$^R$ with pDN232; plasmid-cured strain was isolated by plating on medium with 8ADP | Present study |
| WWM987 | Δhpt::PmcrB-tetR, ΔmtmCB2 | WWM60 was transformed to Pur$^R$ with pDN223; plasmid-cured strain was isolated by plating on medium with 8ADP | Present study |
| WWM988 | Δhpt::PmcrB-tetR, ΔmtmCB1, ΔmtmCB2 | WWM60 was transformed to Pur$^R$ with pDN236; plasmid-cured strain was isolated by plating on medium with 8ADP | Present study |
| WWM989 | Δhpt::PmcrB-tetR, ΔmtmCB1, | WWM60 was transformed to Pur$^R$ with pDN237; plasmid-cured strain was isolated | Present study |

TABLE 6-continued

List of *Methanosarcina acetivorans* strains used in this study

| Strain | Genotype | Construction details | Source |
|---|---|---|---|
| WWM990 | Δhpt::PmcrB-tetR, ΔmtmCB1, ΔmtmCB2, ssuC::mtmCB1 | by plating on medium with 8ADP WWM988 was transformed to Pur[R] with pDN239; plasmid-cured strain was isolated by plating on medium with 8ADP | Present study |
| WWM991 | Δhpt::PmcrB-tetR, ΔmtmCB1, ΔmtmCB2, ssuC::mtmCB2 | WWM988 was transformed to Pur[R] with pDN241; plasmid-cured strain was isolated by plating on medium with 8ADP | Present study |

1. Guss AM, Rother M, Zhang JK, Kulkarni G, Metcalf WW (2008) New methods for tightly regulated gene expression and highly efficient chromosomal integration of cloned genes for *Methanosarcina* species. *Archaea* 2(3):193-203.

Genome Sequencing and Analysis

Genomic DNA from *M. acetivorans* was extracted using a protocol described previously. Boccazzi P, Zhang J, Metcalf W W (2000) Generation of dominant delectable darkers for resistance to pseudomonic acid by cloning and mutagenesis of the ileS gene from the archaeon *Methanosarcina barkeri* Fusaro. *J Bacteriol* 182(9):2611-2618. DNA libraries were prepared with the Hyper Library construction kit (Kapa Biosystems, Wilmington, Mass.) and quantified using qPCR. All libraries were sequenced on one lane of an Illumina MiSeq v2 (Illumina, San Diego, Calif.) at the Roy J. Carver Biotechnology Center, University of Illinois Urbana-Champaign using a 500cycles v2 sequencing kit (Illumina, San Diego, Calif.). Trimmed, paired end 250 nt reads were mapped to the *M. acetivorans* reference genome (NC_003552) using default parameters for breseq v0.25. Barrick J E, et al. (2014) Identifying structural variation in haploid microbial genomes from short-read resequencing data using breseq. *BMC Genomics* 15(1):1039. Trimmed genome sequencing reads have been deposited in the Sequenced Reads Archive (SRA) at the National Center for Biotechnology Information (NCBI) under accession number PRJNA352863.

We claim:

1. A method of homology directed repair-assisted engineering in an archaeon comprising: (i) delivering one or more vectors comprising a genetic engineering cassette comprising a first inducible promoter operably linked to one or more sgRNA sequences, a homologous recombination editing template comprising two homology arms with a deletion portion, a substitution portion comprising a single nucleotide polymorphism, or an insertion portion between the two homology arms, wherein the two homology arms have homology to an archaeon nucleic acid molecule, and a nucleic acid molecule encoding a Type II Cas9 protein operably linked to a second inducible promoter to archaeon host cells; and (ii) isolating transformed archaeon host cells.

2. The method of claim 1, wherein the one or more vectors comprise a counter-selectable marker and the method further comprises curing the transformed archaeon host cells of the one or more vectors by subjecting the transformed archaeon host cells to a counter-selection technique.

3. The method of claim 1, wherein the Type II Cas9 protein comprises a bacterial Cas 9 protein.

4. The method of claim 1, wherein the deletion portion, the substitution portion, or the insertion portion between the two homology arms further comprises a restriction endonuclease site.

5. The method of claim 1, wherein the first inducible promoter is a methanogen promoter, and wherein the archaeon nucleic acid molecule is a methanogen nucleic acid molecule.

6. The method of claim 1, wherein the first inducible promoter is a methanogen promoter and wherein the second inducible promoter is a methanogen or promoter.

7. The method of claim 1, wherein the one or more vectors further comprise a methanogen origin of replication.

8. The method of claim 1, wherein the one or more vectors further comprise a selection marker, a counter-selection marker, or both a selection marker and a counter-selection marker.

9. The method of claim 1, wherein the homologous recombination editing template comprises two homology arms with a deletion portion such that one or more nucleic acid bases are deleted from the archaeon nucleic acid molecule.

10. The method of claim 1, wherein the homologous recombination editing template comprises two homology arms with an insertion portion such that one or more nucleic acid bases are inserted into the archaeon nucleic acid molecule.

11. The method of claim 1, wherein the archaeon is a methanogen.

12. The method of claim 1, wherein two or more sgRNA sequences are present in the genetic engineering cassette.

13. The method of claim 1, wherein the archaeon is *Methanosarcina*.

* * * * *

SEQUENCE LISTING

<160> NUMBER OF SEQ ID NOS: 52

<210> SEQ ID NO 1
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 1
ttttaataaa ttaaggagga aattcatatg gataagaaat actcaatagg ct            52

<210> SEQ ID NO 2
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 2
catacattat acgaagttat caagaagctt tcagtcacct cctagctgac t             51

<210> SEQ ID NO 3
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 3
tccttttgga gccttttttt ttcgaagttt aaacatccat cctgtgcagg tagt          54

<210> SEQ ID NO 4
<211> LENGTH: 30
<212> TYPE: DNA
<213> ORGANISM: Artificial Sequence

```
<220> FEATURE:
<223> OTHER INFORMATION: Synthetic oligonucleotide

<400> SEQUENCE: 4
gcggccgcga ataaattgct tcttccgagt                                     30

<210> SEQ ID NO 5
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 5
tctcctccga ttgtttttaa aggcggccgc ggcgattgcg aatataagag a              51

<210> SEQ ID NO 6
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 6
ggccgcgatc gccggcgcgc ctgcaggttt aaacgcaatg gacgttcgat tgta          54

<210> SEQ ID NO 7
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 7
tcctttggga gccttttttt ttcgaagttt aaacggcgat tgcgaatata agag          54

<210> SEQ ID NO 8
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 8
gcggccgcag ctgaacttcg gctatcag                                       28

<210> SEQ ID NO 9
<211> LENGTH: 59
<212> TYPE: DNA
<213> ORGANISM: Artificial Sequence
<220> FEATURE:
<223> OTHER INFORMATION: Synthetic oligonucleotide

<400> SEQUENCE: 9
gggtactcgg ctgatagccg aagttcagct gcggccgcta cgaagataga tacggccag    59

<210> SEQ ID NO 10
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 10
ggccgcgatc gccggcgcgc ctgcaggttt aaaccgatgg catctataag gctg          54
```

```
<210> SEQ ID NO 11
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 11
ggacgcatcg tggccggatc ttgcggccgc agtaccgaac atagatagag            50

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 12
cttgtattct aagccgaaag                                             20

<210> SEQ ID NO 13
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 13
tcaggtcgaa ctttcggctt agaatacaag attttgagtt gcgatcgcgt tg         52

<210> SEQ ID NO 14
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 14
cgataccgtc aaaacttcat ttttaatttt tgcggccgca gcgccaatct ccagaaaatg  60

<210> SEQ ID NO 15
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 15 cctttggag ccttttttt tcgaagttta aaccatctgt cctcatgcaa ggtg          54

<210> SEQ ID NO 16
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 16
cctattgaca ttatcacaaa gggcctctcc gttgcctcag caaagggtgt tg          52

<210> SEQ ID NO 17
<211> LENGTH: 22
<212> TYPE: DNA
<213> ORGANISM: Artificial Sequence
<220> FEATURE:
<223> OTHER INFORMATION: Synthetic oligonucleotide
```

```
<400> SEQUENCE: 17
gttgcctcag caaagggtgt tg                                           22

<210> SEQ ID NO 18
<211> LENGTH: 56
<212> TYPE: DNA
<213> ORGANISM: Artificial Sequence
<220> FEATURE:
<223> OTHER INFORMATION: Synthetic oligonucleotide

<400> SEQUENCE: 18
gccgcgatcg ccggcgcgcc tgcaggttta aacctcccta ccaatctccg ataacc      56

<210> SEQ ID NO 19
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 19
tggttaccca ggccgtgccg gcacgttaac catctgtcct catgcaaggt gc          52

<210> SEQ ID NO 20
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 20
cacacttgca tcggatgcag cccggttaac tacatgaggg ctgaaaagcc g           51

<210> SEQ ID NO 21
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 21 cctttggag ccttttttt tcgaagttta acattctct cctctggcag aaca           54

<210> SEQ ID NO 22
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 22
gtcatcccgg caaaataaac                                              20

<210> SEQ ID NO 23
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 23
gatttattga gtttattttg ccgggatgac catcgggttg tagaatgcaa tg          52

<210> SEQ ID NO 24
```

```
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 24
gatgttgttg gcgcgcctgc aggtttaaac gtcccaggga taaactaaat tc          52

<210> SEQ ID NO 25
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 25
ccttttggag cctttttttt tcgaagttta aacatggctg tttcaggttg tcc         53

<210> SEQ ID NO 26
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 26
gaagtatgcc atctcactgc                                              20

<210> SEQ ID NO 27
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 27
taaattatta gcagtgagat ggcatacttc tcgggctcag cgtagagtaa c           51

<210> SEQ ID NO 28
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 28
gatgttgttg gcgcgcctgc aggtttaaac cgcatacaat gaggggcaag g           51

<210> SEQ ID NO 29
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 29
atccgctgca aactgccata tgg                                          23

<210> SEQ ID NO 30
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 30
```

```
ctgagggaat cgcaacaaaa cgg                                              23

<210> SEQ ID NO 31
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 31
aggttgcgca cagttagccc agg                                              23

<210> SEQ ID NO 32
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 32
aaggaagaag ctcgaagacc tgg                                              23

<210> SEQ ID NO 33
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 33
ctgaggcaga aagatctctg cgg                                              23

<210> SEQ ID NO 34
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 34
gaggaggcac atctccgtac cgg                                              23

<210> SEQ ID NO 35
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 35
tgaactctct gatggcaccg cgg                                              23

<210> SEQ ID NO 36
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 36
gattgcacgc tgaccgagag ggg                                              23

<210> SEQ ID NO 37
<211> LENGTH: 23
<212> TYPE: DNA
```

<213> ORGANISM: Artificial Sequence
<220> FEATURE:
<223> OTHER INFORMATION: Synthetic oligonucleotide

<400> SEQUENCE: 37
gagagtcacg accatccata agg                                    23

<210> SEQ ID NO 38
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 38
ttatctggac aaacgtcagt cgg                                    23

<210> SEQ ID NO 39
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 39
atccgctgca aactgccata tgg                                    23

<210> SEQ ID NO 40
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 40
aaggaagaag ctcgaagacc tgg                                    23

<210> SEQ ID NO 41
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 41
aaggaagaag ctcgaagaac tag                                    23

<210> SEQ ID NO 42
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 42
aggttgcgca cagttagccc agg                                    23

<210> SEQ ID NO 43
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 43
aggctgtgta cagttaaccc agg                                    23

<210> SEQ ID NO 44
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 44
ctgaggcaga aagatctctg cgg                                           23

<210> SEQ ID NO 45
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 45
ctgaggtaga aagaccctca gca                                           23

<210> SEQ ID NO 46
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 46
gaggaggcac atctccgtac cgg                                           23

<210> SEQ ID NO 47
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 47
aaggaggcac atctctgtac atg                                           23

<210> SEQ ID NO 48
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 48
ccctcagcca                                                          10

<210> SEQ ID NO 49
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 49
ctgaagaagc c                                                        11

<210> SEQ ID NO 50
<211> LENGTH: 11
<212> TYPE: DNA
<213> ORGANISM: Artificial Sequence
<220> FEATURE:

```
<223> OTHER INFORMATION: Synthetic oligonucleotide

<400> SEQUENCE: 50
gtggacgaag c                                                          11

<210> SEQ ID NO 51
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 51 ccctgacaa                                                              9

<210> SEQ ID NO 52
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 52 tcctgc                                                                 6
```